United States Patent
Lee

(10) Patent No.: US 11,566,220 B2
(45) Date of Patent: Jan. 31, 2023

(54) CELL LINE CONSECUTIVELY EXPRESSING HLA-G PROTEIN AND METHOD FOR PREPARING THE SAME

(71) Applicants: STEMMEDICARE CO., LTD., Seoul (KR); Jang Ho Lee, Seoul (KR)

(72) Inventor: Jang Ho Lee, Seoul (KR)

(73) Assignee: STEMMEDICARE CO., LTD., Seoul (KR)

( * ) Notice: Subject to any disclaimer, the term of this patent is extended or adjusted under 35 U.S.C. 154(b) by 0 days.

(21) Appl. No.: 16/486,882

(22) PCT Filed: Apr. 26, 2019

(86) PCT No.: PCT/KR2019/005072
§ 371 (c)(1),
(2) Date: Aug. 19, 2019

(87) PCT Pub. No.: WO2019/209068
PCT Pub. Date: Oct. 31, 2019

(65) Prior Publication Data
US 2021/0147797 A1    May 20, 2021

(30) Foreign Application Priority Data
Apr. 26, 2018  (KR) .................. 10-2018-0048484

(51) Int. Cl.
| | | |
|---|---|---|
| *C12N 5/073* | (2010.01) | |
| *C12N 5/0775* | (2010.01) | |
| *A61K 8/98* | (2006.01) | |
| *A61K 35/28* | (2015.01) | |

(52) U.S. Cl.
CPC ............ *C12N 5/0605* (2013.01); *A61K 8/981* (2013.01); *A61K 35/28* (2013.01); *C12N 5/0662* (2013.01); *C12N 2500/76* (2013.01); *C12N 2502/025* (2013.01); *C12N 2523/00* (2013.01); *C12N 2527/00* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 9,284,528 B2 | 3/2016 | Chuang | |
| 2008/0248005 A1* | 10/2008 | Phan | C12N 5/0655 435/395 |
| 2010/0221268 A1* | 9/2010 | Parolini | C12N 5/0605 435/366 |

FOREIGN PATENT DOCUMENTS

| | | |
|---|---|---|
| CN | 1995334 | 7/2007 |
| JP | 2013-544250 | 12/2013 |
| KR | 10-2017-0121205 | 11/2017 |

OTHER PUBLICATIONS

Ding et al. "Characterization of HLA-G and related immunosuppressive effects in human umbilical cord stroma-derived stem cells." Cell Transplantation 25.2 (2016): 217-228. (Year: 2016).*
Choi, Jong Ho, et al., "Effect of mesenchymal stem cells and extracts derived from the placenta on trophoblast invasion and immune responses." *Stem Cells and Development* 23.2 (2013): 132-145.
Ding. Dah-Ching, et al. "Characterization of HLA-G and related immunosuppressive effects in human umbilical cord stroma-derived stem cells." *Cell Transplantation* 25.2 (2016): 217-228.
Helige, C., et al. "Trophoblastic invasion in vitro and in vivo: similarities and differences." *Human Reproduction* 23.10 (2008): 2282-2291.
JP 2013-544250, English Machine Translation, dated Apr. 22, 2021.

* cited by examiner

*Primary Examiner* — Emily A Cordas
(74) *Attorney, Agent, or Firm* — ParkerHighlander, PLLC

(57) ABSTRACT

The disclosure relates to the establishment of a cell line having immune tolerance property using an optimal temperature profiling technique under a human body-like environment, and use thereof.
The stem cell line exhibits immune tolerance property as they consecutively secret and express HLA-G proteins, and the culture medium of the stem cells contains a large amount of proteins capable of recovering various physiological functions and extracellular vesicles, and thus, the novel cell line or a culture medium thereof can be effectively used in various industries such as medicines and cosmetics.

18 Claims, 11 Drawing Sheets

[FIG. 1]
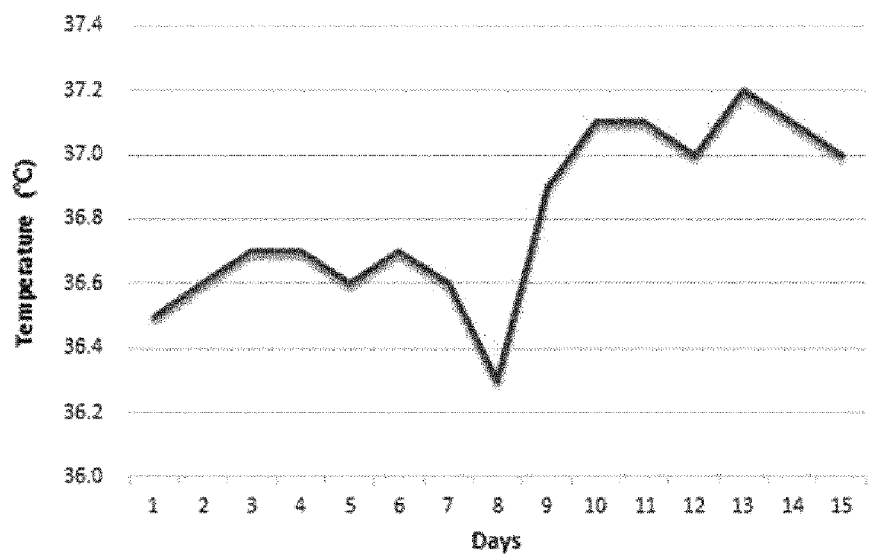
[FIG. 2]
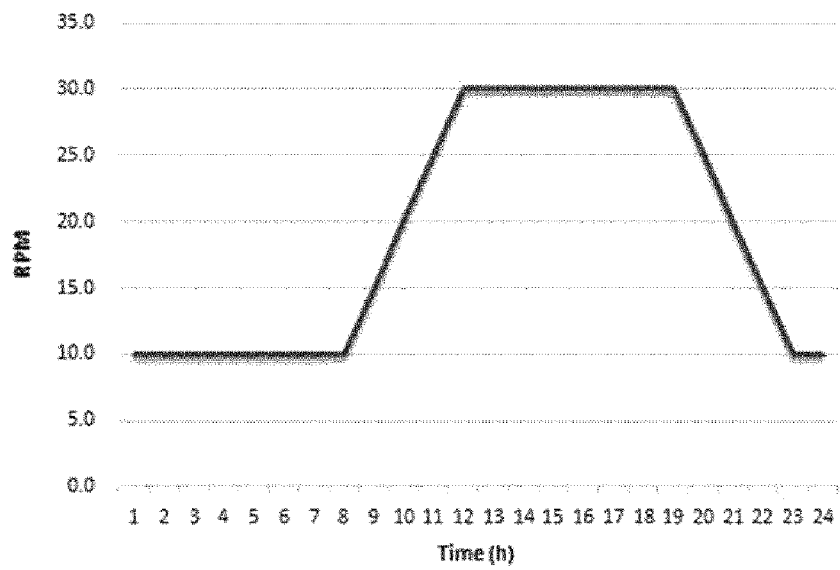

[FIG. 3]
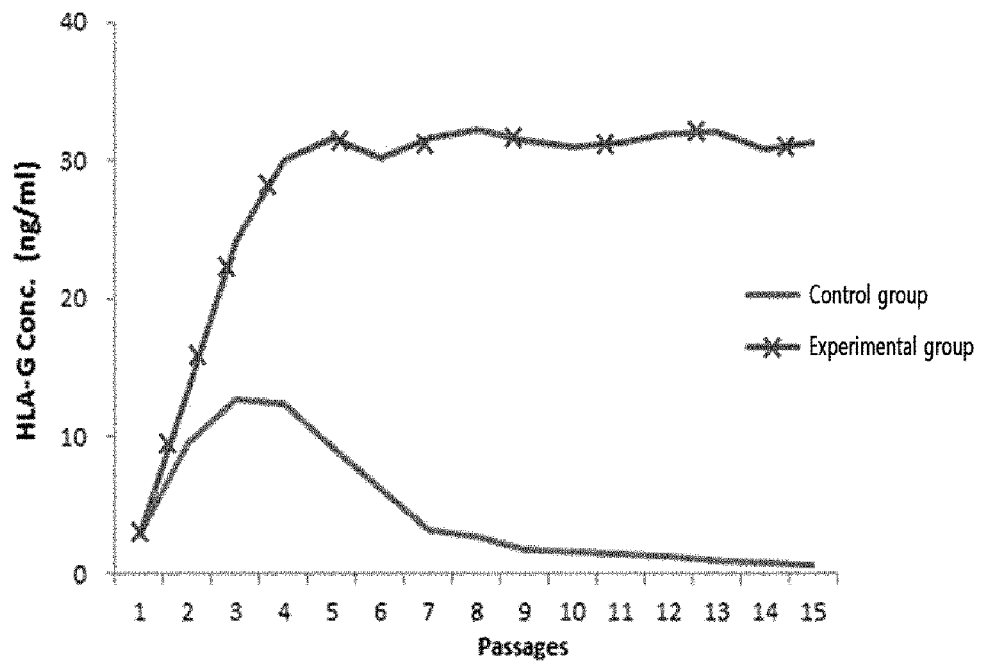
[FIG. 4]
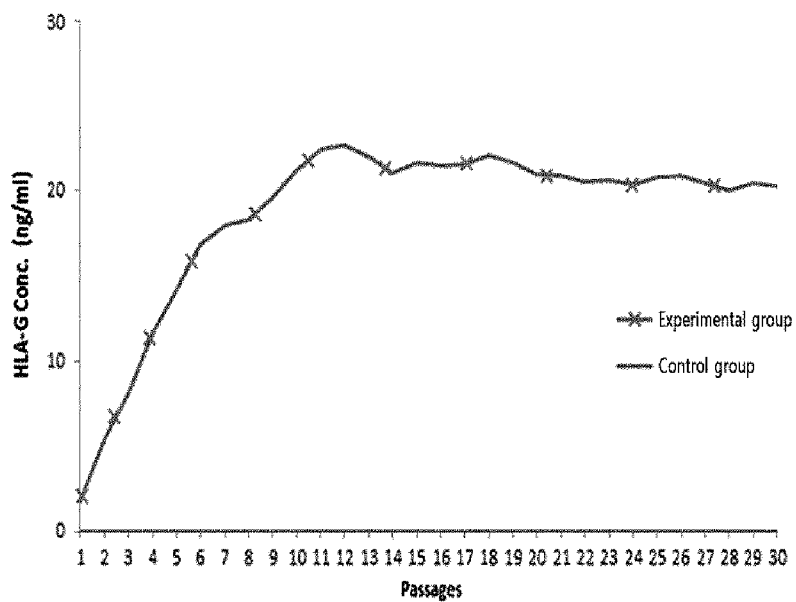

[FIG. 5]
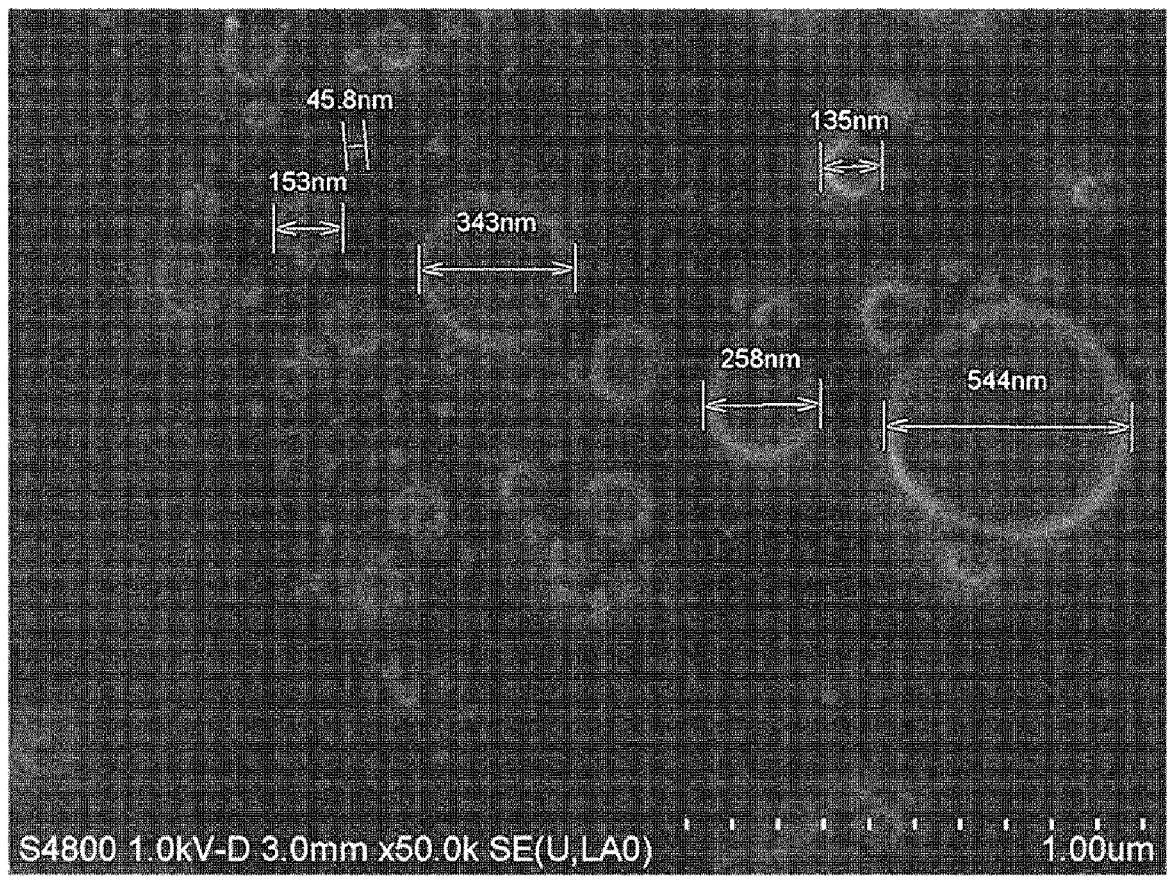

[FIG. 6]
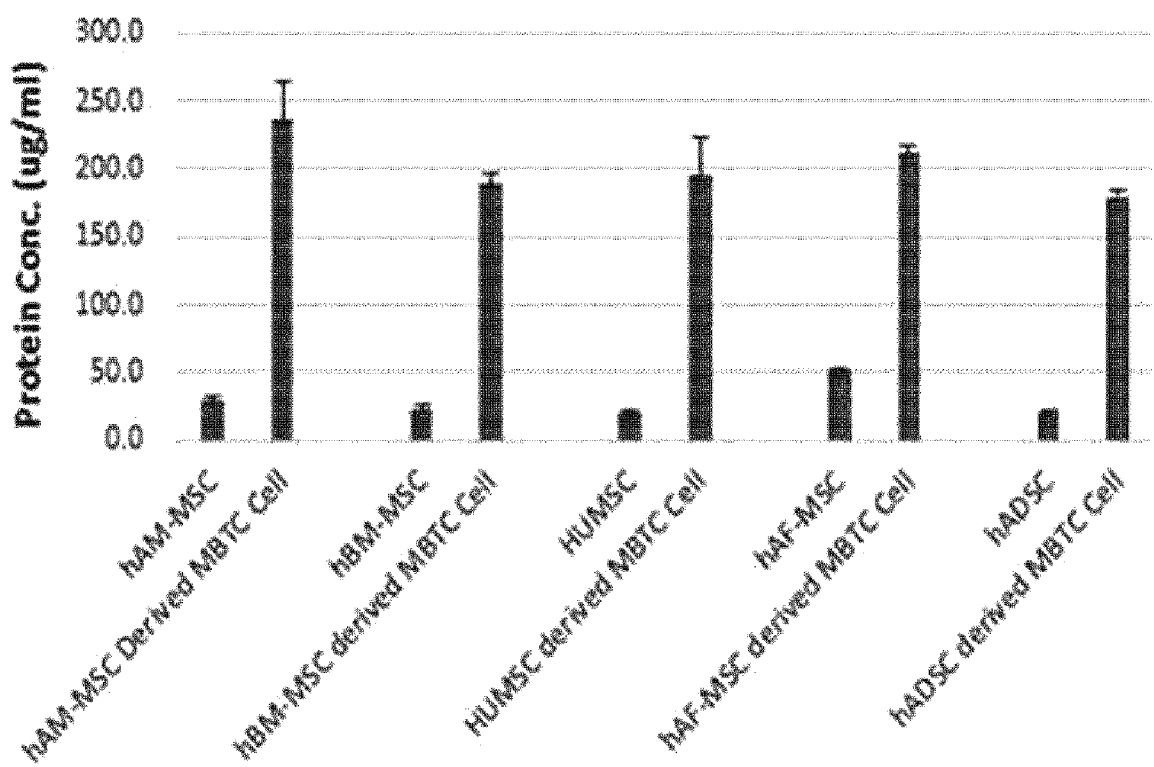

[FIG. 7]
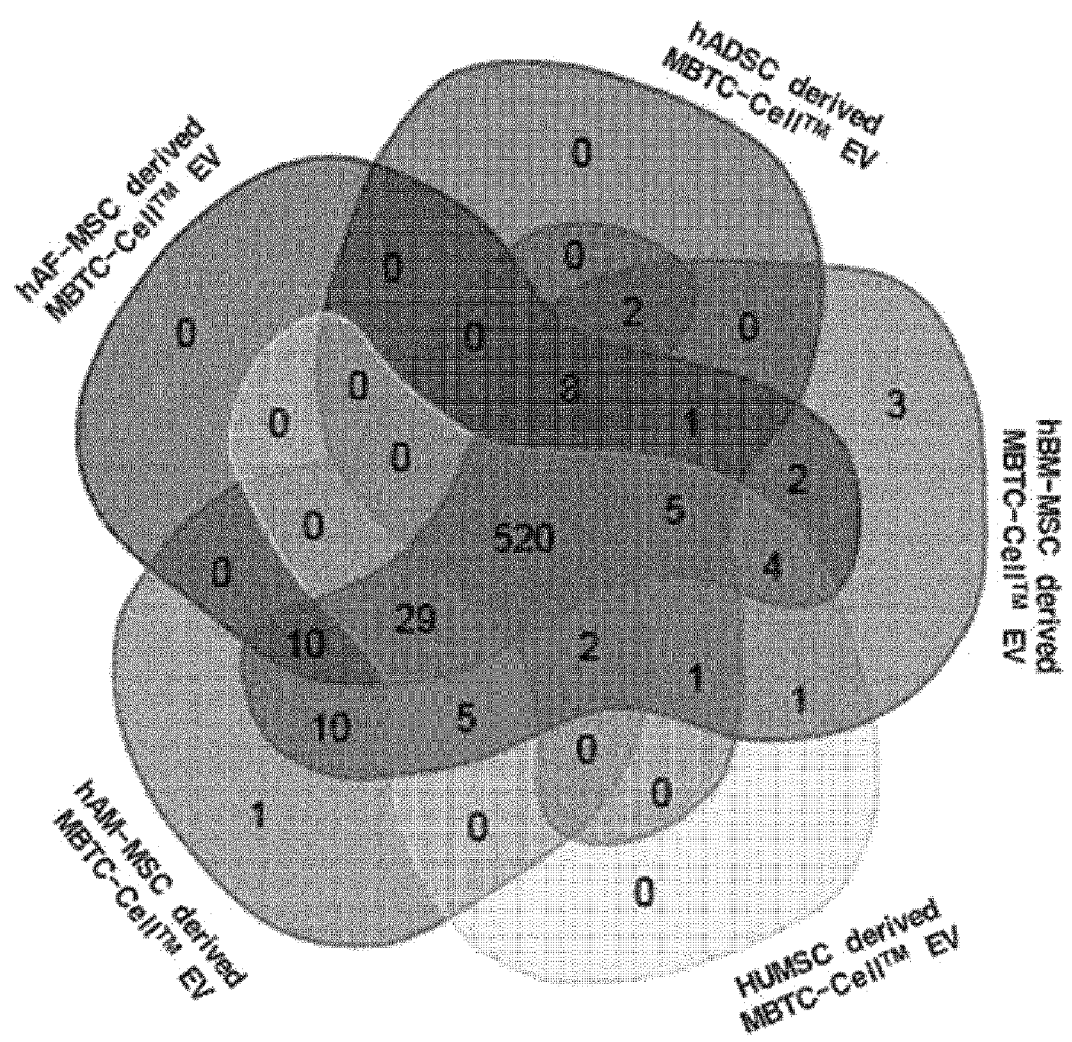

[FIG. 8]
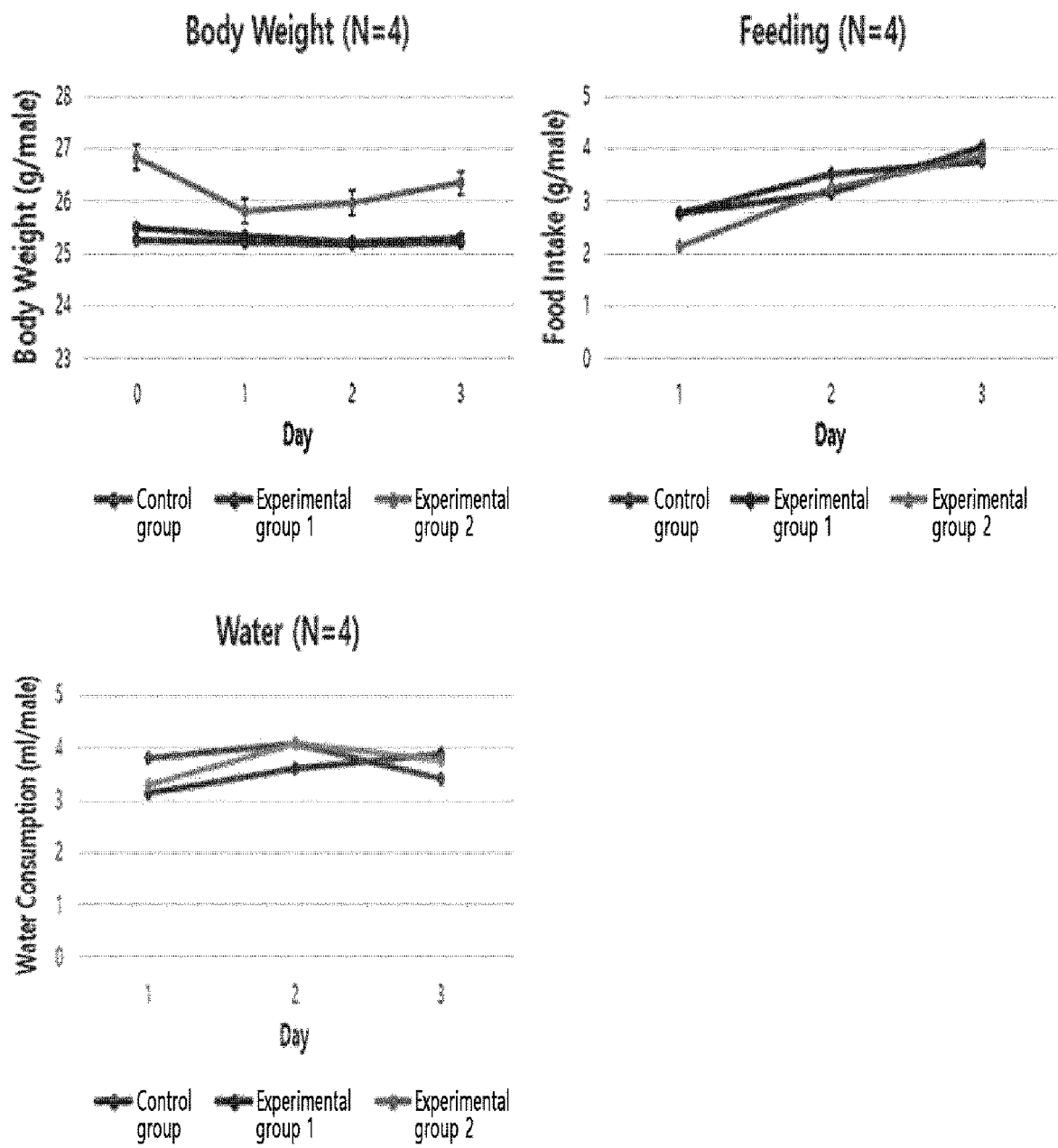

[FIG. 9]
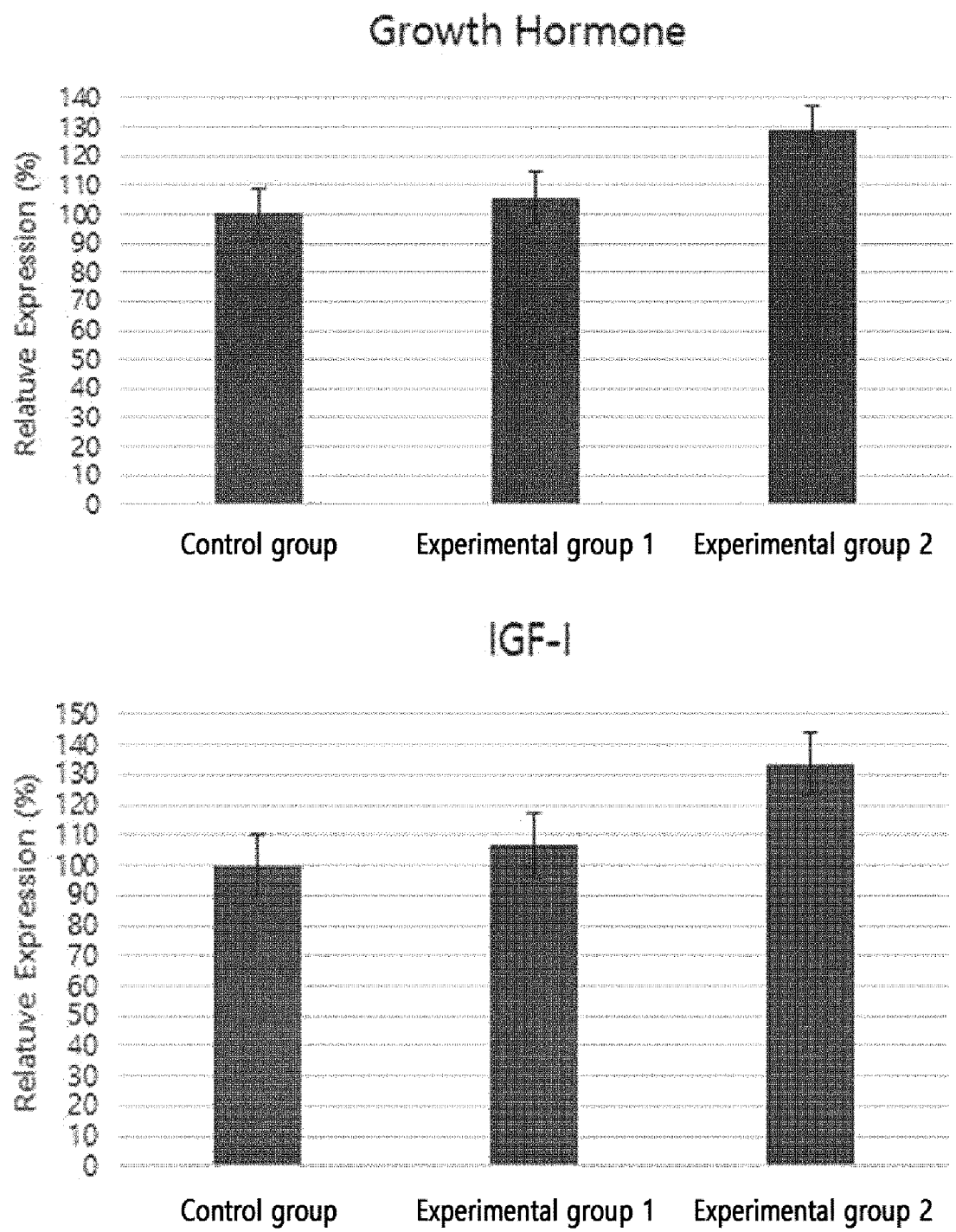

[FIG. 10]
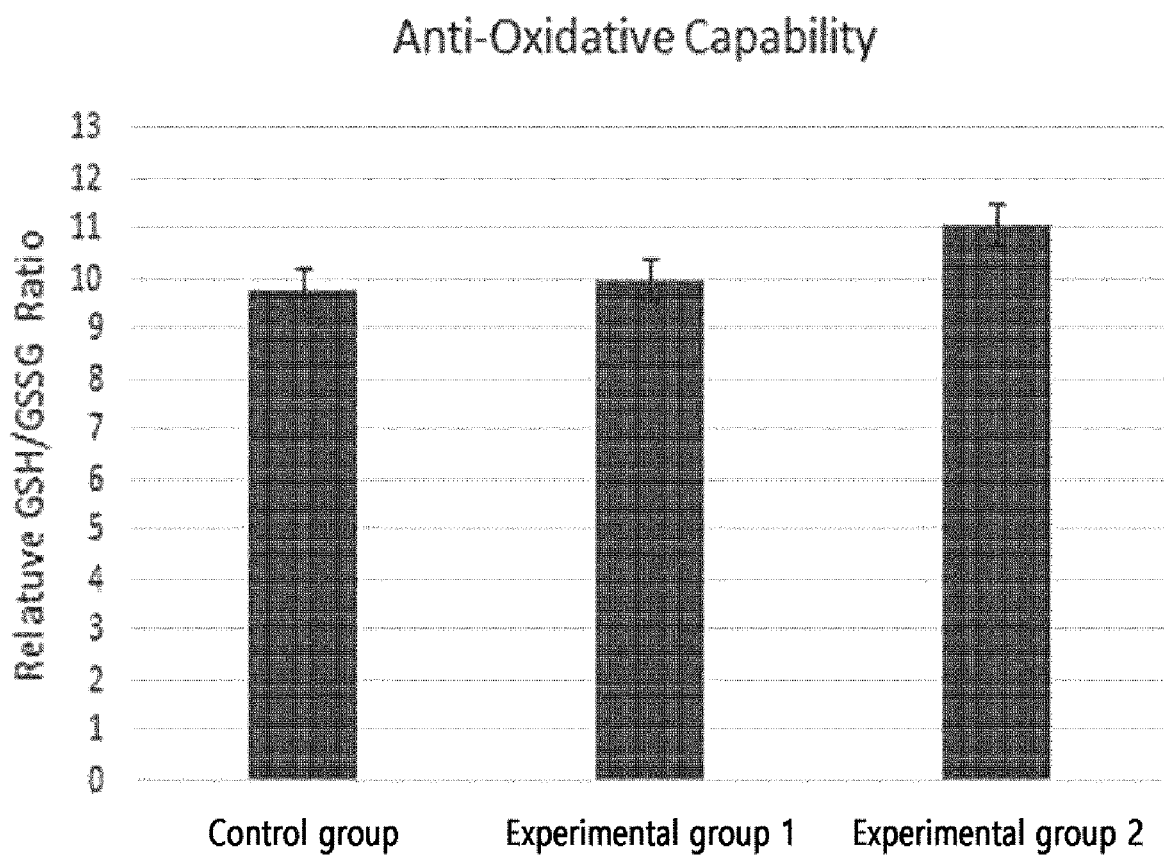

[FIG. 11]
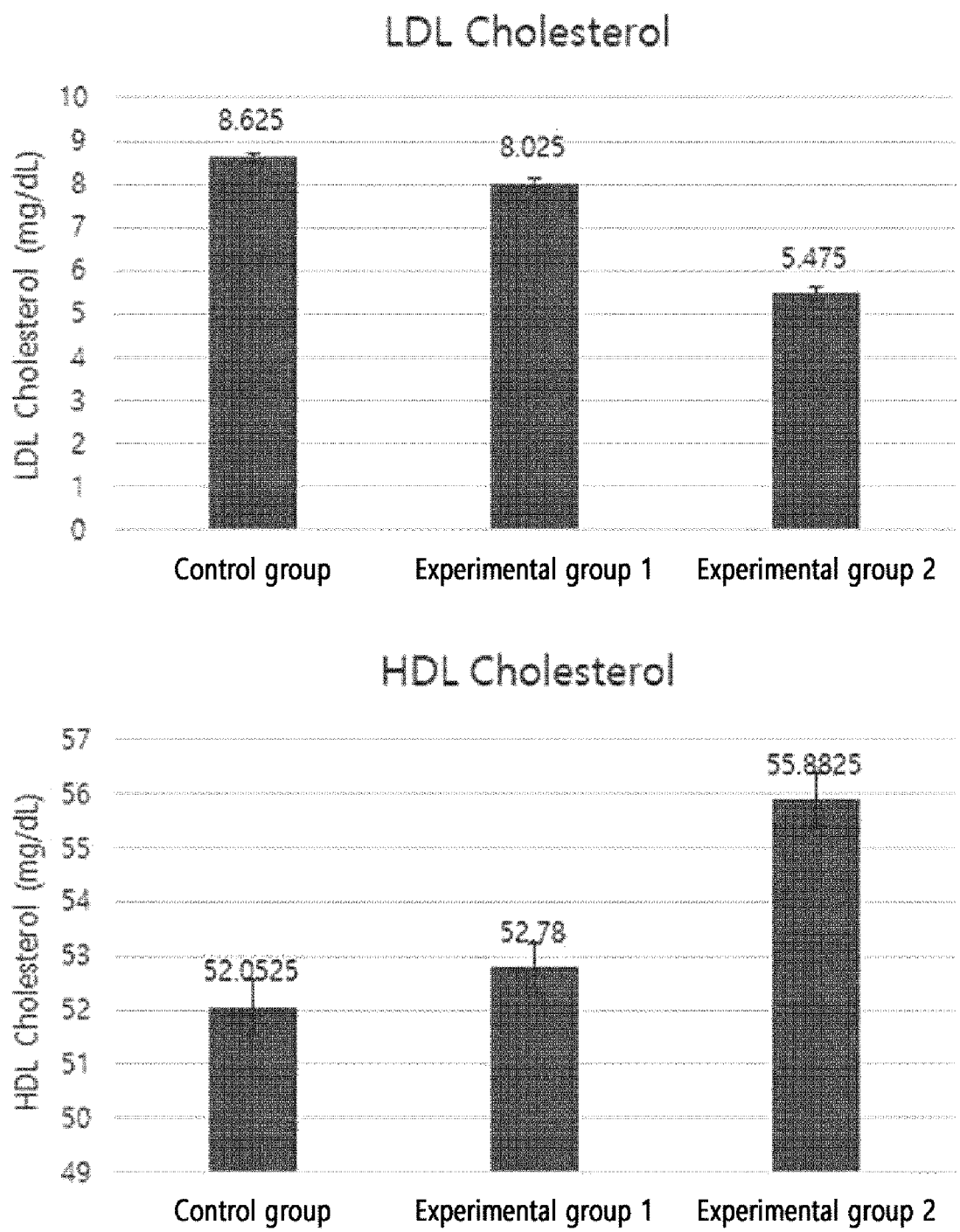

[FIG. 12]
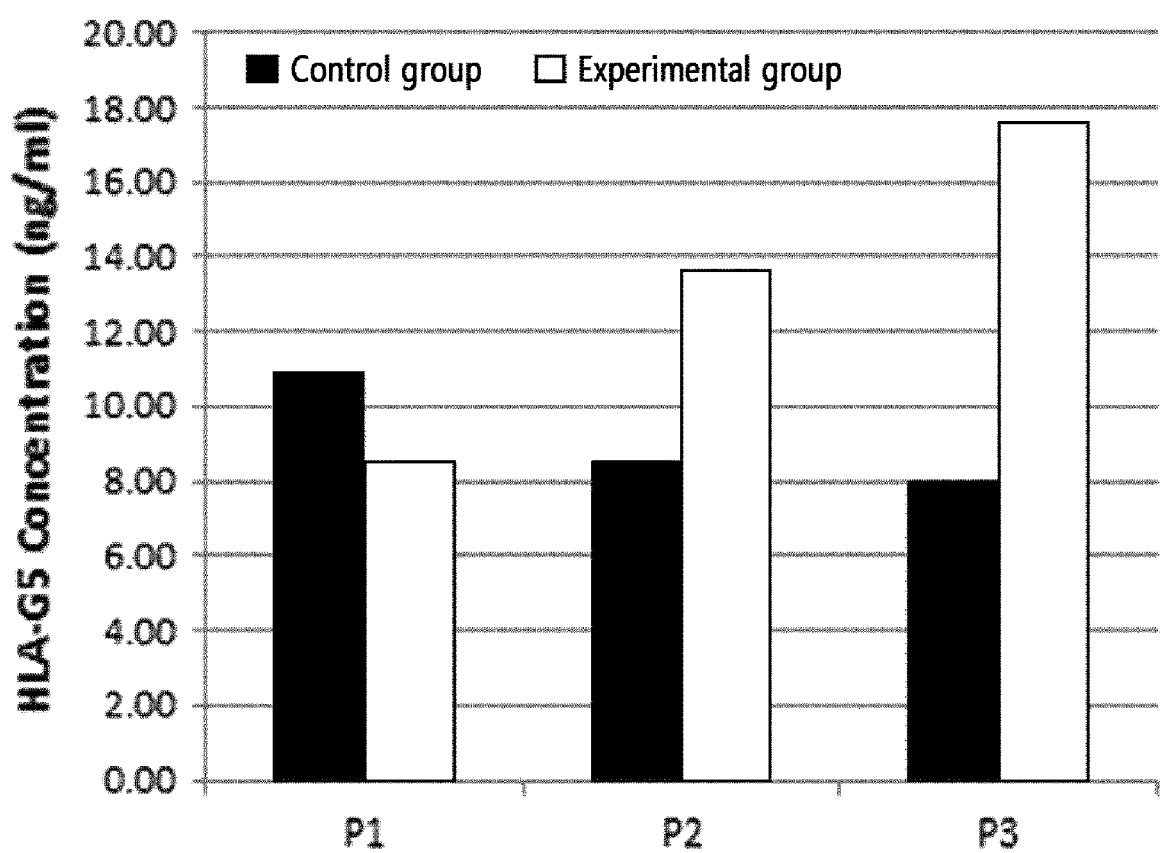

[FIG. 13]
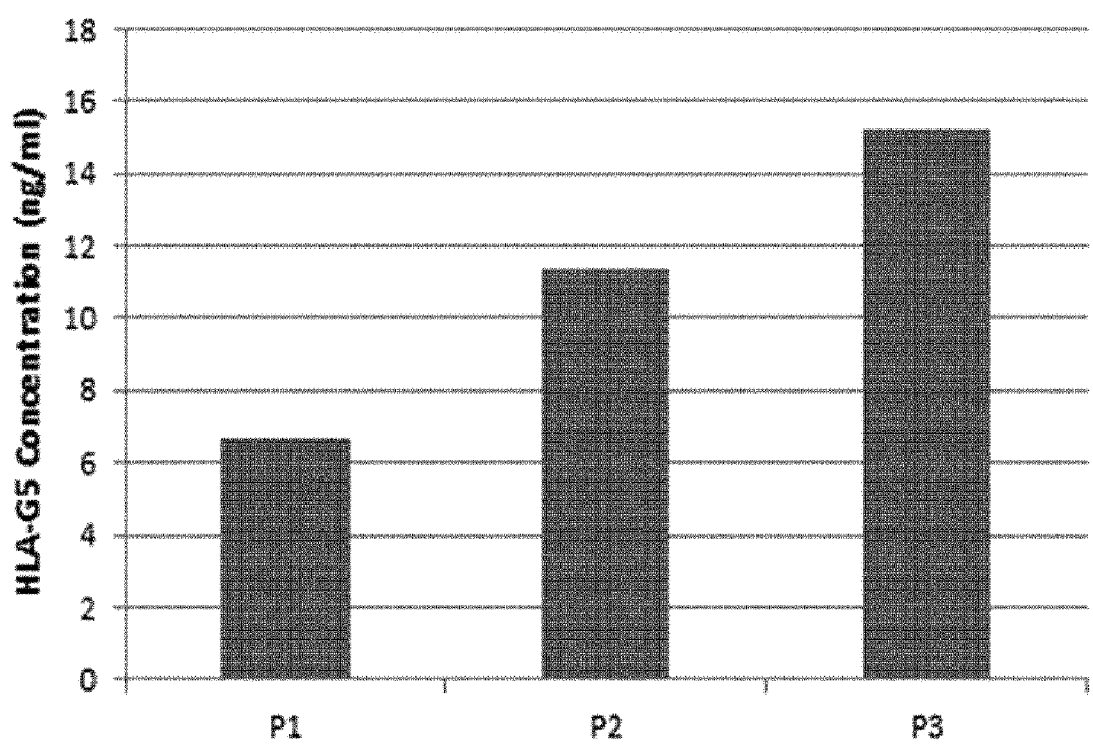

CELL LINE CONSECUTIVELY EXPRESSING HLA-G PROTEIN AND METHOD FOR PREPARING THE SAME

This application is a national phase application under 35 U.S.C. § 371 of International Application No. PCT/KR2019/005072, filed Apr. 26, 2019, which claims priority to Korean Application No. 10-2018-0048484, filed Apr. 26, 2018. The entire text of each of the above referenced disclosures is specifically incorporated herein by reference.

TECHNICAL FIELD

The present invention relates to a cell line consecutively secreting and expressing HLA-G proteins and a method for preparing the same. Specifically, the present invention relates to a method for preparing trophoblast cells consecutively secreting and expressing HLA-G proteins; a method for preparing stem cells consecutively secreting and expressing HLA-G proteins; stem cells consecutively secreting and expressing HLA-G proteins, prepared by the aforementioned preparation method; a method for preparing a culture medium of stem cells consecutively secreting and expressing HLA-G proteins; a culture medium of stem cells consecutively secreting and expressing HLA-G proteins, prepared by the aforementioned preparation method; and an anti-aging or antioxidant composition comprising the culture medium as an active ingredient.

BACKGROUND ART

Cell therapeutic agents can be used as a fundamental therapeutic method for recovering the function and tissue of a damaged cell by manipulating and culturing the cells collected from a patient or other people in vitro and injecting them into the patient. Therefore, development of cell therapeutic agents for the diseases which are impossible or difficult to treat by existing treatment methods, such as neurological diseases, pulmonary diseases, liver diseases, and cancers, is actively carried out. In particular, there has been a great interest worldwide in clinical trials using stem cells having self-renewal capability and differentiation capability into other cells, as more than thousands of cases are under progress.

However, since stem cells are acquired through long-term in vitro culture and then injected into patients, there is a risk of mutation of stem cells into cancer cells and tumor formation during these processes and a risk caused by heterologous proteins such as FBS used for cell storage and culture, and there are problems associated with immunogenicity caused by major histocompatibility complex (MHC) mismatches, and immune rejection that requires short-term or long-term follow-up due to the immunogenicity. Accordingly, these risks and problems bring about the biggest technical difficulty in the commercialization of stem cell therapeutics agents. In addition, with respect to cell transplantation and transplantation of extracellular vesicles such as exosomes and microvesicles secreted from the cells, various immunomodulatory and inhibitory drugs have been developed in order to solve immune rejections caused by immunogenicity such as cell therapeutic agents, but they can only be a partial solution for the problems.

Meanwhile, it has been known that a culture medium of stem cells contains various growth factors and cytokines produced from stem cells, and therefore, its commercial use as pharmaceuticals and cosmetics is rapidly increasing. As related prior arts, there have been developed a cosmetic composition for improving scalp comprising a stem cell culture medium (Korean Patent Application Publication No. 10-2017-0132460) and a method for producing a culture supernatant of mesenchymal stem cells having exceptional tissue regeneration capacity, exceptional disease healing action, or high physiological activity (Korean Patent Application Publication No. 10-2017-0121205).

However, stem cell culture media are currently produced by culturing stem cells isolated from human body fat, etc., using a general cell culture method, and substances that can be included in the culture media are limited, and accordingly, various effects cannot be achieved.

DISCLOSURE

Technical Problem

The present inventor has made extensive efforts to develop a novel stem cell that does not show immune rejection caused by immunogenicity and a culture medium including various useful ingredients derived from the stem cell, and as a result, they have prepared a novel stem cell line consecutively secreting and expressing HLA-G proteins, which are known to exhibit immune tolerance, and have confirmed that the culture medium of the stem cell line contains various extracellular vesicles and proteins and has direct antioxidant and anti-aging effects, thereby completing the present invention.

Technical Solution

It is one object of the present invention to provide a method for preparing trophoblast cells consecutively secreting and expressing HLA-G proteins, including:
culturing trophoblast cells under a human body-like culture condition; and
sub-culturing the cultured trophoblast cells.

It is another object of the present invention to provide a method for preparing stem cells consecutively secreting and expressing HLA-G proteins, including:
co-culturing trophoblast cells and stem cells consecutively secreting and expressing HLA-G proteins; and
sub-culturing the cultured stem cells.

It is still another object of the present invention to provide stem cells consecutively secreting and expressing HLA-G proteins, prepared by the aforementioned method for preparing stem cells consecutively secreting and expressing HLA-G proteins.

It is still further another object of the present invention to provide a method of preparing a culture medium of stem cells consecutively secreting and expressing HLA-G proteins.

It is still further another object of the present invention to provide a culture medium of stem cells consecutively secreting and expressing HLA-G proteins, prepared by the aforementioned method for preparing a culture medium of stem cells consecutively secreting and expressing HLA-G proteins.

It is still further another object of the present invention to provide an anti-aging or antioxidant composition including the aforementioned culture medium as an active ingredient.

Advantageous Effects

The novel trophoblast cell line and the stem cell line established in the present invention can exhibit immune tolerance property as they consecutively secret and express HLA-G proteins, and the culture medium of the stem cells contains a large amount of proteins capable of recovering various physiological functions and extracellular vesicles, and thus, the novel cell line or the culture medium thereof can be effectively used in various industries such as medicines and cosmetics.

BRIEF DESCRIPTION OF DRAWINGS

FIG. 1 is a graph showing the temperature condition used for culture in order to produce cells that consecutively secret and express HLA-G proteins and have immune tolerance property. Herein, the basal body temperature method optimized for a human body-like environment was applied.

FIG. 2 is a graph showing the micro vibrating condition used for culture in order to produce cells that consecutively secret and express HLA-G proteins and have immune tolerance property. The graph reflects on the pattern of daily activities of the human body.

FIG. 3 is a graph showing the concentration of HLA-G proteins present in the culture medium of the trophoblast cells. The control group was a culture medium of cells cultured by a conventional method, and the Experimental group was a culture medium of cells cultured under the aforementioned temperature and vibrating conditions.

FIG. 4 is a graph showing the concentration of HLA-G proteins present in the culture medium of the novel stem cell line (MBTC-Cell™) which consecutively secrets and expresses HLA-G proteins and exhibits immune tolerance property. The control group was a culture medium of human-derived mesenchymal stem cells cultured by a conventional method, and the Experimental group was a culture medium of MBTC-Cell™.

FIG. 5 is a scanning electron microscope image of MBTC-Cell™-derived culture medium showing extracellular vesicles (MBTC-EV™), such as microvesicles and exosomes of various sizes, and proteins.

FIG. 6 is a graph showing the total amount of a protein contained in the MBTC-Cell™-derived culture medium. Specifically, hAM-MSC, hBM-MSC, HUMSC, hAF-MSC, and hADSC refer to human amniotic membrane, bone marrow, umbilical cord blood, amniotic fluid, and adipose-derived mesenchymal stem cells cultured by conventional methods, respectively. Further, hAM-MSC-derived MBTC-Cell™, hBM-MSC-derived MBTC-Cell™, HUMSC-derived MBTC-Cell™, hAF-MSC-derived MBTC-Cell™, and hADSC-derived MBTC-Cell™ refer to human amniotic membrane, bone marrow, umbilical cord blood, amniotic fluid, and adipose-derived mesenchymal stem cells co-cultured with the trophoblast cells under the aforementioned temperature and vibrating conditions, respectively.

FIG. 7 is a Venn diagram resulting from the qualitative analysis of the kinds of proteins contained in the MBTC-Cell™-derived culture medium.

FIG. 8 is a graph comparing the results of the measurement of the body weight, the amount of water and feed intake of the mice administered with the MBTC-Cell™-derived culture medium. The control group was a 0.9% saline solution, Experimental Group 1 was a culture medium of human-derived mesenchymal stem cells cultured by a conventional method, and Experimental Group 2 was a group administered with the MBTC-Cell™-derived culture medium.

FIG. 9 is a graph showing the anti-aging effect of the MBTC-Cell™-derived culture medium, comparing the expression levels of growth hormone and insulin-like growth factor 1 (IGF-1). The control group was a 0.9% saline solution, Experimental Group 1 was a culture medium of human-derived mesenchymal stem cells cultured by a conventional method, and Experimental Group 2 was a group administered with the MBTC-Cell™-derived culture medium.

FIG. 10 is a graph showing the antioxidant effect of the MBTC-Cell™-derived culture medium, comparing the ratio of GSH/GSSH (glutathione/glutathione disulfide). The control group was a 0.9% saline solution, Experimental Group 1 was a culture medium of human-derived mesenchymal stem cells cultured by a conventional method, and Experimental Group 2 was a group administered with the MBTC-Cell™-derived culture medium.

FIG. 11 is a graph showing the effect of recovering the macrophage-phagocytosis function of MBTC-Cell™-derived culture medium, comparing the blood LDL-cholesterol concentration and the HDL-cholesterol concentration. The control group was a 0.9% saline solution, Experimental Group 1 was a culture medium of human-derived mesenchymal stem cells cultured by a conventional method, and Experimental Group 2 was a group administered with the MBTC-Cell™-derived culture medium.

FIG. 12 is a graph showing the concentration of HLA-G5 proteins present in the culture medium of trophoblast cells. The control group was a culture medium of cells cultured by a conventional method, and the Experimental group was a culture medium of cells cultured under the aforementioned temperature and vibrating conditions of FIGS. 1 and 2, respectively.

FIG. 13 is a graph showing the concentration of HLA-G5 proteins present in the culture medium of the novel stem cell line (MBTC-Cell™), which consecutively secrets and expresses HLA-G proteins and has immune tolerance property.

DETAILED DESCRIPTION OF EMBODIMENTS

In order to achieve the objects above, one aspect of the present invention provides a method for preparing trophoblast cells consecutively secreting and expressing HLA-G proteins, including:

culturing trophoblast cells under a human body-like culture condition, wherein the human body-like culture condition includes a temperature condition varied within a range of 36.3° C. to 37.2° C., a vibrating incubating condition varied within a range of 10 RPM to 30 RPM, and a condition using a cell culture plate containing an extracellular matrix; and sub-culturing the cultured trophoblast cells.

The novel trophoblast cells consecutively secreting and expressing HLA-G proteins are cultured in accordance with various physiological characteristics such as growth environment, temperature change, and motility of cells in the human body, and may thus have a feature of consecutively secreting and expressing HLA-G proteins, which can exhibit immune tolerance property.

As used herein, "HLA-G protein" is a protein referred to as human leukocyte antigen G or HLA-G histocompatibility antigen class G. The HLA-G protein plays a role in immune tolerance by decreasing toxicity of immune cells and promoting differentiation of regulatory T cells due to its specificity of low polymorphism and action on immune cells. In this regard, the immune response triggered by T cells is relatively reduced by decreasing the activity of activated T cells and promoting proliferation of T regulatory cells at the same time. In addition, it plays a key role in immune tolerance which can protect the human body from attack by all kinds of immune cells, such as a decrease in dendritic cell maturation and activity of NK cells, and inhibition of B cell activity. Thus, HLA-G-expressed cells and extracellular vesicles have immune tolerance property and can be securely protected from the immune system of a patient by suppressing local or systemic immune rejection, when applied to human body. There are seven types of HLA-G proteins. Among these, HLA-G1/2/3/4 proteins are expressed on the cell membrane and cell surface, and HLA-G5/6/7 proteins are found in the form of a single molecule secreted outside the cell. In one embodiment of the invention, the HLA-G proteins may be, but are not limited to, HLA-G5.

As used herein, the term "trophoblast cells" are a type of cells forming placenta, which provide signaling related to embryo development and nutrients to inner cell mass at the early stage of its development, and give rise to a successful conception by inducing immune tolerance to protect the fertilized embryo from the mother's immune system at the initial stage of implantation, thereby playing an important role in the maintenance of pregnancy and fetal development. It is known that the role of trophoblast cells is attributed to the expression of HLA-G proteins. In one embodiment of the invention, the HLA-G proteins may be, but are not limited to, HLA-G5.

In the present invention, the human body-like culture condition may be a temperature condition varied within a range of 36.3° C. to 37.2° C., and the temperature condition may be a temperature change condition over a 15-day period based on the basal body temperature method.

As used herein, the term "basal body temperature method" refers to a pregnancy control method using the basal body temperature of a woman. The basal body temperature refers to the body temperature at the moment when all activities other than breathing stop, and is conventionally the temperature attained immediately after awakening. Depending on the menstrual cycle, the low-temperature period and the high-temperature period of the basal body temperature are repeated at intervals of two weeks. In particular, the high-temperature period is maintained for 2 weeks after ovulation, which seems to have the lowest temperature (36.3° C.), and when the menstruation starts, the body temperature drops again. Since the basal body temperature varies from person to person, the temperature condition can be appropriately adjusted by those skilled in the art, as long as the temperature varies within the range of 36.3° C. to 37.2° C.

Further, the human body-like culture condition may be a vibrating incubating condition varied within a range of 10 RPM to 30 RPM, and the vibrating incubating condition may be a vibrating culture condition over a 24-hour period. This may reflect on the pattern of daily activities of a person, and such pattern of activities varies from person to person, the vibrating culture condition can be appropriately adjusted by those skilled in the art, as long as the frequency varies within 10 RPM to 30 RPM.

In addition, the human body-like culture condition may be a condition using a cell culture plate containing an extracellular matrix. In a specific embodiment, the extracellular matrix may be coated on a cell culture plate.

As used herein, the term "extracellular matrix" is a cell-generated substance that serves to protect and support cells by filling the space between cells and tissues. Specifically, the extracellular matrix may be one or more selected from the group consisting of collagen, fibronectin, and procollagen.

Specifically, the extracellular matrix is prepared by the steps of:
(a) inoculating fibroblasts at a density of 18,000 cells/cm$^2$ to 22,000 cells/cm$^2$;
(b) culturing the fibroblasts in a serum-free medium; and
(c) obtaining a fibroblast culture medium after culturing for 114 hours to 126 hours,
wherein the serum-free medium may contain 15% (v/v) to 25% (v/v) of human mesenchymal stem cell-derived proteins. When the fibroblasts are cultured under the above conditions, the extracellular matrix can be obtained at the maximum production amount.

As used herein, the term "human mesenchymal stem cell-derived protein" refers to a protein secreted from human mesenchymal stem cells. As a specific embodiment, it may be a culture medium derived from human mesenchymal stem cells containing human mesenchymal stem cell-derived proteins. In the present specification, the human mesenchymal stem cell-derived protein can be used interchangeably with "hPC".

Specifically, the protein may include growth factors or cytokines derived from human mesenchymal stem cells. More specifically, it may include AR, BDNF, bFGF, BMP-4, BMP-5, BMP-7, b-NGF, EGF-R, FGF-4, FGF-7, GDF-15, GDNF, HGF, IGFBP-1, IGFBP-2, IGFBP-3, IGFBP-4, IGFBP-6, IGF-1, insulin, MCSF, MCSF-R, NGF-R, NT-3, NT-4, OPG, PDGF-AA, PlGF, SCF, SCF-R, TGF-α, TGF-β1, VEGF, VEGF-R3, ICAM-1, G-CSF, IL-1α, IL-2, IL-5, IL-6, IL-8, IL-11, MCP-1, MIG, MIP-1a, MIP-b, MIP-d, TIMP-1, TIMP-2, TNFα, TNFβ, TNF-R1, or TNF-R11, but is not limited thereto.

Further, the human mesenchymal stem cell-derived protein may be prepared by the steps of:
(a) inoculating human mesenchymal stem cells at a density of 18,000 cells/cm$^2$ to 22,000 cells/cm$^2$;
(b) culturing the stem cells in a serum-free medium; and
(c) obtaining a stem cell culture medium after culturing for 114 hours to 126 hours. When the human mesenchymal stem cells are cultured under the above conditions, the human mesenchymal stem cell-derived proteins can be obtained at the maximum production amount.

For the purpose of the present invention, the sub-culture may be performed for 5 passages or more, and specifically for 5 passages to 15 passages. The secretion and expression of HLA-G proteins from the trophoblast cells are markedly increased when the cells are sub-cultured for 5 passages or more.

In addition, the HLA-G proteins can be maintained at 30 ng/ml or more in the culture medium of trophoblast cells consecutively secreting and expressing the HLA-G proteins of the present invention, which are prepared by the above-mentioned steps. At this time, the HLA-G proteins may be secreted outside the trophoblast cells, and may be HLA-G5 when secreted outside the cells, but is not limited thereto.

In one specific embodiment of the present invention, the extracellular matrix, such as procollagen, fibronectin, and collagen, was prepared by culturing human fibroblasts using a medium supplemented with 20% hPC, and subsequently the trophoblast cells were cultured under the conditions of the basal body temperature method and pattern of activities of human using a culture plate coated with the extracellular matrix prepared above, and as a result, when the subculture was performed for 5 passages or more, it was confirmed that the concentration level of HLA-G proteins in the culture medium of trophoblast cells was increased, so that the level thereof was maintained at 30 ng/ml or more, thereby establishing a novel trophoblast cell line consecutively secreting and expressing HLA-G proteins (see FIGS. 1 to 3).

In addition, it was confirmed that the trophoblast cells prepared by the above method secreted a HLA-G5 protein, thus confirming that HLA-G proteins could be secreted outside the cells, and it was also confirmed that the amount of a HLA-G5 was increased as the subculture was performed, thereby confirming that the trophoblast cells could consecutively secret and express HLA-G5 (see FIG. 12).

These results suggest that the trophoblast cell line can be effectively used for the development of a cell therapeutic agent or a novel cell line which requires immune tolerance property, as they consecutively secret and express HLA-G proteins, which show immune tolerance property.

Another aspect of the present invention provides a method for preparing stem cells consecutively secreting and expressing HLA-G proteins, including:

co-culturing stem cells with trophoblast cells consecutively secreting and expressing HLA-G proteins; and sub-culturing the cultured stem cells.

Still another aspect of the present invention provides stem cells consecutively secreting and expressing HLA-G proteins prepared by the aforementioned method for preparing stem cells consecutively secreting and expressing HLA-G proteins.

Herein, the "HLA-G protein" and "trophoblast cells" are as described above.

The novel stem cell line consecutively secreting and expressing HLA-G proteins of the present invention (named as "MBTC-Cell™" in the present specification) may have a feature of consecutively secreting and expressing HLA-G proteins, which can exhibit immune tolerance property, by co-culturing with trophoblast cells consecutively secreting and expressing HLA-G proteins. Further, it can express large amounts of proteins related to immune tolerance, proteins related to recovering proteasome function, proteins related to recovering autophagy function, proteins related to recovering macrophage-phagocytosis function, or proteins related to maintaining intracellular signaling homeostasis, and thus, the stem cell and a culture medium thereof can be effectively used for the treatment of various diseases caused by the inactivation of the above-mentioned functions without immune rejection.

In the present invention, the stem cell may be a mesenchymal stem cell.

As used herein, the term "mesenchymal stem cell" is a cell that serves as an original source to make cartilage, bone, fat, bone marrow stroma, muscle, and nerve. In adults, it is usually found in bone marrow, but can also exist in other tissues, such as umbilical cord blood, peripheral blood, fat, or amniotic fluid, and refers to stem cells that can be obtained therefrom. Specifically, the mesenchymal stem cell may be derived from fat, bone marrow, umbilical cord blood, amniotic fluid, or amniotic membrane, but is not limited thereto. Further, the mesenchymal stem cell may be derived from a mammal including human.

For the purpose of the present invention, the stem cells may be co-cultured with the trophoblast cells consecutively secreting and expressing HLA-G proteins. The co-culture is a means for culturing two different types of cells in one culture medium, in which cells do not make contact with each other, but are affected by substances secreted from each cell by sharing the culture medium. The stem cells of the present invention may also have a feature of consecutively secreting and expressing HLA-G proteins outside the cells, while interacting with the trophoblast cells consecutively secreting and expressing HLA-G proteins via co-culture. Herein, the HLA-G proteins may be, but are not limited to, HLA-G5.

The co-culture may be carried out in a medium including a mixture in which human mesenchymal stem cell-derived proteins and plant extracts are mixed at a ratio of 1:0.5 to 1:1.5.

Herein, the "human mesenchymal stem cell-derived protein" is as described above. In the present invention, the plant extract may be a *Aspalathus linearis* leaf extract, *Thuja occidentalis* leaf extract, *Melaleuca alternifolia* (tea tree) leaf extract, *Rosmarinus officinalis* (rosemary) leaf extract, *Centella asiatica* extract, *Salvia officinalis* (sage) leaf extract, *Thymus vulgaris* (thyme) extract, *Melissa officinalis* leaf extract, *Hyssopus officinalis* extract, *Origanum majorana* leaf extract, *Glycyrrhiza uralensis* (licorice) root extract, *Angelica gigas* root extract, *Cnidium officinale* root extract, *Paeonia lactiflora* (peonia) root extract, *Perilla frutescens* leaf extract, *Houttuynia cordata* extract, *Camellia sinensis* leaf extract, *Poria cocos* extract, *Panax ginseng* root extract, moms alba bark extract, *Citrus aurantifolia* (lime) fruit extract, *Citrus limon* (lemon) fruit extract, *Vitis vinifera* (grape) fruit extract, *Cucumis melo* (melon) fruit extract, *Vaccinium angustifolium* (blueberry) fruit extract, *Prunus mume* fruit extract, *Coffee arabica* (coffee) seed extract, *Sapindus mukorossi* fruit extract, *Citrus aurantium dulcis* (orange) fruit extract, *Ananas sativus* (pineapple) fruit extract, or a combination thereof, but is not limited thereto.

In addition, the mixture may include a mixture in which the human mesenchymal stem cell-derived proteins and the plant extracts are mixed at a ratio of 1:05 to 1:1.5, specifically at a ratio of 1:1, but is not limited thereto.

For the purpose of the present invention, the sub-culture may be carried out for 10 passages to 30 passages. When the stem cells are sub-cultured within the above range, they can maintain a healthy state, and also, the secretion and expression of HLA-G proteins are remarkably increased.

Further, the HLA-G proteins secreted and expressed by the stem cells prepared by the above-mentioned steps may be present in a culture supernatant and an extracellular vesicle. The HLA-G proteins may be, but are not limited to, HLA-G5.

Furthermore, the HLA-G protein may be maintained at 20 ng/ml or more, specifically at 20 ng/ml to 30 ng/ml, but is not limited thereto.

In one specific embodiment of the present invention, the novel trophoblast cells and mesenchymal stem cells consecutively secreting and expressing HLA-G proteins were co-cultured by adding mixtures, in which 30 kinds of mixed plant extracts and hPC were mixed in a ratio of 1:1, to the medium in an amount of 1.0 wt % to 10 wt %, and as a result, when the sub-culture was performed for 10 passages or more, the secretion amount of HLA-G proteins was increased, so that the level thereof was maintained at 20 ng/ml or more, thereby establishing the novel stem cell line consecutively secreting and expressing HLA-G proteins (see FIG. 4).

Further, in one embodiment of the present invention, it was confirmed that the stem cells secreted HLA-G5 proteins, thus confirming that HLA-G proteins could be secreted outside the cells, and it was also confirmed that the amount of HLA-G5s was increased as the subculture was performed, thereby confirming that the stem cells could consecutively secret and express HLA-G5 (see FIG. 13).

These results suggest that the stem cell line can be effectively used for the development of a cell therapeutic agent or a novel cell line which requires immune tolerance, and for the development of an extracellular vesicle therapeutic agent and an immunosuppressant having immune tolerance as it consecutively secret and express HLA-G proteins, which shows immune tolerance property.

Still further another aspect of the present invention provides a method of preparing a culture medium of mesenchymal stem cells consecutively secreting and expressing HLA-G proteins, including:

preparing mesenchymal stem cells consecutively secreting and expressing HLA-G proteins by the aforementioned method for preparing stem cells consecutively secreting and expressing HLA-G proteins; and obtaining a culture supernatant by the steps of:

(a) inoculating the mesenchymal stem cells obtained at the time of sub-culturing during the preparation of the mesenchymal stem cells at a density of 18,000 cells/cm$^2$ to 22,000 cells/cm$^2$; and (b) culturing the mesenchymal stem cells in a serum-free medium for 114 hours to 126 hours.

Still further another aspect of the present invention provides a culture medium of stem cells consecutively secreting and expressing HLA-G proteins, prepared by the aforementioned method for preparing a culture medium of mesenchymal stem cells consecutively secreting and expressing HLA-G proteins.

Herein, the "human mesenchymal stem cell-derived protein" is as described above.

In the present invention, the culture medium of stem cells prepared above may contain extracellular vesicles.

As used herein, the term "culture medium" refers to a medium capable of supporting the growth and survival of stem cells in vitro, and is intended to include all conventional media known in the art, which are suitable for the culture of stem cells.

In one embodiment of the present invention, the culture medium of the prepared stem cells may include HLA-G proteins secreted and expressed outside the cells from the stem cells and an extracellular vesicle containing the HLA-G proteins. Herein, the HLA-G proteins may be, but are not limited to, a HLA-G5.

As used herein, the term "extracellular vesicle" is a heterogeneous group containing various physiologically active substances secreted from cells in the phospholipid bilayer membrane, and there are various kinds depending on the origin and size. Most of the cells are involved in various biological reactions by protecting and transporting physiologically active molecules, such as active proteins and lipids, through the extracellular vesicles and delivering them to other cells. Since these extracellular vesicles also have the phospholipid bilayer membrane, which is almost the same as the cell membrane of its parent cell, the exogenous antigens of the parent cell present in this membrane act as an immunogen, which can cause an immune response. However, the extracellular vesicles included in the stem cell culture medium prepared according to the present invention also express HLA-G proteins capable of controlling such an immune response, and thus have an advantage of suppressing an immune response through an immune tolerance mechanism when applied to patients.

Specifically, the extracellular vesicle may be at least one selected from the group consisting of an apoptotic body, a microvesicle and an exosome, and more preferably, it may be at least one selected from the group consisting of a microvesicle and an exosome, but is not limited thereto.

The term "apoptotic body" has a diameter of 1,000 nm or more, and is a vesicle generated in the form of a cell nucleus fragment or organelles attached to the cell membrane when apoptosis occurs.

The term "exosome" has a diameter of about 30 nm to 150 nm, and is a vesicle which is secreted outside of the cells in the form of an endosome bound with a multivesicular body through a fusion mechanism with the plasma membrane within a cell.

In addition, the term "microvesicle" has a diameter of 50 nm to 1,000 nm, and is a vesicle which is directly secreted outside of shed from the cell membrane.

In the present invention, the prepared culture medium of stem cells may have an increased total protein content. Specifically, the prepared culture medium of stem cells has a total protein content higher than the culture medium of stem cells that do not consecutively secret and express HLA-G proteins or the culture medium of mesenchymal stem cells that are not co-cultured with trophoblast cells consecutively secreting and expressing HLA-G proteins.

Herein, the protein may be a protein related to immune tolerance, a protein related to recovering proteasome function, a protein related to recovering autophagy function, an antioxidant protein related to recovering macrophage-phagocytosis function, or a protein related to maintaining intracellular signaling homeostasis.

In addition, the protein related to immune tolerance may specifically be fascin, galectin-3, galectic-3-binding protein, peptidylprolyl cis-trans isomerase B, forkhead box P3, interleukin-10, or transforming growth factor beta-1, but is not limited thereto, as long as it exhibits immune tolerance property.

Accordingly, the culture medium of stem cells prepared according to the present invention contains a large amount of the above-mentioned proteins exhibiting immune tolerance, and thus can be effectively used for the prevention and/or treatment of autoimmune-related diseases. In addition, the culture medium can be effectively used for suppressing immune rejection, which may occur during transplantation of autologous and allogeneic cells, tissues, organs or extracellular vesicles for the purpose of restoration, regeneration and treatment of cells and tissues.

In addition, the protein related to recovering proteasome function may specifically be 26S protease regulatory subunit 8, 26S proteasome non-ATPase regulatory subunit 2, 26S proteasome non-ATPase regulatory subunit 3, 26S proteasome non-ATPase regulatory subunit 6, heat shock 70 kDa protein 1L, 26S proteasome regulatory subunit S10B, E3 ubiquitin-protein ligase BRE1B, heat shock 70 kDa protein 6, heat shock 70 kDa protein 90Bb, heat shock protein beta-1, heat shock-related 70 kDa protein 2, heat shock-related 70 kDa protein 8, 26S proteasome non-ATPase regulatory subunit 1, proteasome subunit alpha type-1, proteasome subunit alpha type-2, proteasome subunit alpha type-5, proteasome subunit beta type-4, proteasome subunit alpha type-6, proteasome subunit alpha type-7, proteasome subunit beta type-5, proteasome subunit beta type-8, proteasome subunit beta type-1, proteasome subunit beta type-2, proteasome subunit beta type-3, or ubiquitin-like modifier-activating enzyme 1, but is not limited thereto, as long as it exhibits a feature of recovering proteasome function.

Therefore, the culture medium of stem cells prepared according to the present invention contains a large amount of the above-described proteins showing a feature of recovering proteasome function, and thus can be effectively used for the prevention and/or treatment of proteasome dysfunction-related diseases.

Further, the protein related to recovering autophagy function may specifically be Bcl2-associated agonist of cell death, NF-kappa-B essential modulator, insulin, pro-epidermal growth factor, somatotropin, transforming growth factor beta-2, interleukin-1 beta, lysosomal associated membrane protein 2, autophagy-related protein 16-2, autophagy-related protein 9A, or mannose-6 phosphate, but is not limited thereto, as long as it shows a feature of recovering autophagy function.

Therefore, the culture medium of stem cells prepared according to the present invention contains a large amount of the above-described proteins showing a feature of recovering autophagy function, and thus can be effectively used for the prevention and/or treatment of autophagy dysfunction-related diseases.

Furthermore, the antioxidant protein related to recovering macrophage-phagocytosis function may specifically be glutathione S-transferase omega-1, glutathione reductase, peroxiredoxin-1, peroxiredoxin-2, peroxiredoxin-4, peroxiredoxin-6, or superoxide dismutase, but is not limited thereto, as long as it shows a feature of recovering macrophage-phagocytosis function.

Therefore, the culture medium of stem cells prepared according to the present invention contains a large amount of the above-described proteins showing a feature of recovering macrophage-phagocytosis function, and thus can be effectively used for the prevention and/or treatment of macrophage-phagocytosis dysfunction-related diseases. In addition, the phagocytosis of macrophages is also involved in the elimination of reactive oxygen species/reactive nitrogen species, and thus may be useful for prevention and/or treatment of oxidative stress related-diseases.

Additionally, the protein related to maintaining intracellular signaling homeostasis may specifically be phosphatase and tensin homolog, SH2 (Src homology 2)-containing inositol phosphatase-1, or glycogen synthase kinase 3 beta, but is not limited thereto, as long as it shows a feature of intracellular signaling homeostasis.

Therefore, the culture medium of stem cells prepared according to the present invention contains a large amount of the above-described proteins showing a feature of maintaining intracellular signaling homeostasis, and thus can be effectively used for the prevention and/or treatment of intracellular signaling homeostasis dysfunction-related diseases or intracellular excessive singling-related diseases.

In one specific embodiment of the present invention, it was confirmed that the culture medium of the stem cells consecutively secreting and expressing HLA-G proteins contains large amounts of proteins related to immune tolerance, proteins related to recovering proteasome function, proteins related to recovering autophagy function, proteins related to recovering macrophage-phagocytosis function, or proteins related to maintaining intracellular signaling homeostasis and also contains various extracellular vesicles such as microvesicles and exosomes (see FIGS. 5 to 7 and Tables 5 to 9).

This finding suggests that the aforementioned culture medium can be effectively used for the treatment of diseases caused by such dysfunctions, as it contains large amounts of proteins capable of recovering various body functions.

Still further another aspect of the present invention provides an anti-aging or antioxidant composition including the aforementioned culture medium as an active ingredient.

Herein, the "culture medium" is as described above.

The culture medium of the stem cells consecutively secreting and expressing HLA-G proteins according to the present invention contains large amounts of proteins related to immune tolerance, proteins related to recovering proteasome function, proteins related to recovering autophagy function, proteins related to recovering macrophage-phagocytosis function, or proteins related to maintaining intracellular signaling homeostasis and also contains various extracellular vesicles such as microvesicles and exosomes at the same time, and thus can show advantageous physiological activities such as anti-aging and antioxidant activities.

Specifically, the anti-aging or antioxidant composition may be a health functional food, a cosmetic, a quasi-drug, or a feed composition.

As used herein, the term "health functional food", which has the same meaning as the term "food for special health use (FoSHU)", refers to a food with high effects in medicinal and medical treatment, processed so as to efficiently exhibit a body modulating function as well as to provide nutrients. In the present invention, the health functional food is used interchangeably with a health food or a health supplementary food.

As used herein, the term "cosmetics" refers to goods which are used for a human body in order to add charming of the human body and change the appearance of the human body to be brighter, or to maintain or enhance skin or hair in a healthy state by making the human body clean and beautiful, and have a minor effect on the human body. They are intended to include functional cosmetics that help to whiten the skin, help to improve skin wrinkles, and help to tan the skin beautifully and protect the skin from ultraviolet rays.

As used herein, the term "quasi-drug" refers to a product that is less active than drugs, among the products used for the purpose of diagnosing, treating, improving, alleviating, curing, or preventing a disease of a human or animal. For example, according to the Pharmaceutical Affairs Law, quasi-drugs include products used for the treatment or prevention of a human or animal disease, and products that minimally or indirectly act on the human body, excluding products that are used for drugs.

As used herein, the term "feed" refers to any natural or artificial diet, a single meal, or a component of the single meal, which an animal eats, ingests and digests or which is suitable for eating, ingestion and digestion.

In one specific embodiment of the present invention, when the culture medium of stem cells consecutively secreting and expressing HLA-G proteins administered to mice, it was confirmed that the expression of GF and IGF-1, which are biomarkers related to anti-aging, was increased, the serum GSH/GSSH ratio, which is a typical biomarker related to antioxidation, was increased, and the concentration of serum LDL cholesterol was reduced while increasing the concentration of serum HDL cholesterol (see FIGS. 8 to 11).

These findings suggest that the composition including the culture medium of the present invention exhibits excellent anti-aging and antioxidant effects, and thus can be effectively used in the form of health functional foods, cosmetics, quasi-drugs or feed compositions.

MODE FOR CARRYING OUT THE INVENTION

Hereinafter, the constitution and effect of the present invention will be described in detail by way of Examples.

However, these Examples are given for illustrative purposes only, and the scope of the invention is not intended to be limited by these Examples.

Example 1: Preparation of Extracellular Matrix for Providing In Vivo-Like Cell Culture Environment In order to prepare a novel stem cell line in which immune tolerance property was induced, an attempt was made to provide an in vivo-like environment at the time of culturing cells.

Specifically, human fibroblasts were cultured using proteins secreted from mesenchymal stem cells, and an extracellular matrix (procollagen, fibronectin, collagen) was secreted from the human fibroblasts so that it was directly prepared to be used.

The detailed preparation method is as follows: First, among human amniotic membrane-derived mesenchymal stem cells (SCIENCELL, Cat. #7501), human adipose-derived mesenchymal stem cells (STEMPRO® Human Adipose Derived Stem Cell, INVITROGEN, Cat. #R7788-110), human bone marrow-derived mesenchymal stem cells (SCIENCELL, Cat. #7500), human umbilical cord blood-derived mesenchymal stem cells (SCIENCELL, Cat. #7530) and human amniotic fluid-derived mesenchymal stem cells (ANGIOCRINE, cat. #hAmnio-01), one type of stem cells was inoculated at 20,000 cells/cm$^2$ in DMEM/F12 medium, a serum-free medium and cultured in a 5% $CO_2$ incubator at 37° C. for 120 hours to obtain human mesenchymal stem cell-derived proteins (Human Protein Complex from Human Mesenchymal Stem Cell, hereinafter, referred to as hPC). Thereafter, human fibroblast cells (Human CCD-98sk) were inoculated at 20,000 cells/cm$^2$ in DMEM culture medium supplemented with hPC at concentrations (1.25%, 2.5%, 5%, 10%, 20%) that did not exhibit cytotoxicity and then cultured in a 5% $CO_2$ incubator at 37° C. for 120 hours.

After completion of culture, the contents of procollagen (collagen precursor), fibronectin (cell-binding glycoprotein), and collagen (fibrous protein) were measured according to a known method for each culture supernatant according to the concentration of hPC, and the results are shown in Tables 1 to 3 below.

TABLE 1

Comparison of Production Amount of Procollagen According to hPC Concentration

| hPC Concentration (%, Total protein (μg/mL)) | Procollagen (ng/mL) | | | Average Procollagen (ng/mL, Mean ± S.E.) | % Negative Control |
|---|---|---|---|---|---|
| 0 (0) | 162.17 | 160.87 | 164.25 | 162.43 ± 0.98 | 100.00 ± 0.00 |
| 1.25 (0.625) | 167.56 | 167.11 | 170.39 | 168.35 ± 1.03 | 103.65 ± 0.17 |
| 2.5 (1.25) | 191.38 | 166.84 | 192.44 | 183.55 ± 8.36 | 112.96 ± 4.63 |
| 5.0 (2.5) | 277.34 | 257.76 | 271.93 | 269.01 ± 5.84 | 165.60 ± 3.11 |
| 10.0 (5.0) | 622.07 | 751.34 | 747.01 | 706.81 ± 42.39 | 435.15 ± 26.02 |
| 20.0 (10.0) | 1,786.17 | 2,095.16 | 2,690.04 | 2,190.46 ± 265.24 | 1,347.19 ± 156.44 |

TABLE 2

Comparison of Production Amount of Collagen According to hPC Concentration

| hPC Concentration (%, Total protein (μg/mL)) | Collagen (ng/mL) | | | Average Collagen (ng/mL, Mean ± S.E.) | % Negative Control |
|---|---|---|---|---|---|
| 0 (0) | 144.80 | 134.47 | 143.97 | 140.08 ± 4.31 | 100.00 ± 0.00 |
| 20.0 (10.0) | 3,073.26 | 3,148.36 | 3,128.05 | 3,116.56 ± 22.43 | 2.229.95 ± 83.66 |

TABLE 3

Comparison of Production Amount of Fibronectin According to hPC Concentration

| hPC Concentration (%, Total protein (μg/mL)) | Fibronectin (ng/mL) | | | Average Fibronectin (ng/mL, Mean ± S.E. | % Negative Control |
|---|---|---|---|---|---|
| 0 (0) | 223.01 | 206.47 | 201.36 | 210.28 ± 6.53 | 100.00 ± 0.00 |
| 20.0 (10.0) | 5,261.64 | 5,306.78 | 5,420.74 | 5,329.72 ± 47.34 | 2,540.56 ± 97.18 |

As can be seen from Tables 1 to 3 above, it was confirmed that the amount of procollagen produced from human fibroblasts was increased in proportion to the concentration of hPC added to the medium. Further, it was confirmed that procollagen, collagen, and fibronectin were most produced when the human fibroblasts were cultured in the serum-free culture medium containing 20% hPC.

Thus, the extracellular matrix prepared by the method above was used in the subsequent cell culture.

Example 2: Preparation Method of Trophoblast Cells Consecutively Secreting and Expressing HLA-G In order to prepare a novel stem cell line in which immune tolerance property was induced, HLA-G proteins were used.

The HLA-G protein protects cells from NK cells, and is a protein which functions in immune tolerance and immunomodulation that it does not mediate a homologous immune response by T cells in peripheral blood. It is mainly secreted and expressed in the trophoblast cells that form the placenta and causes immune tolerance to protect the fertilized embryo from the mother's immune system in the early stage of implantation, thereby playing a role in inducing a successful implantation and maintaining normal pregnancy.

Therefore, the present inventor has made an effort to establish a culture condition for trophoblast cells in order to prepare trophoblast cells capable of consecutively secreting and expressing HLA-G proteins by focusing on the features of immune tolerance and various signaling pathways of trophoblast cells, which consecutively secret and express HLA-G proteins at the highest level in the body, and a novel stem cell line having improved signaling capacity by co-culturing stem cells with the established trophoblast cells to induce immune tolerance property.

First, trophoblast cells consecutively secreting and expressing HLA-G proteins were prepared by sub-culture such that immune tolerance could be imparted.

This process was carried out using the basal body temperature method. The basal body temperature refers to the body temperature at the moment when all activities other than breathing stop, and is conventionally the temperature attained immediately after awakening. By measuring the changes in basal body temperature, ovulation time and pregnancy can be predicted in women. In addition, depending on the menstrual cycle, the low-temperature period and the high-temperature period of the basal body temperature are repeated at intervals of two weeks. In particular, the high-temperature period is maintained for 2 weeks after ovulation, which seems to have the lowest temperature (36.3° C.), and when the menstruation starts, the body temperature drops again. The present inventor has noted that such changes in the basal body temperature would be closely related to ovulation, fertilization, pregnancy and implantation and also to the features of trophoblast cells and the body's immune system, which play an important role in the series of these processes.

Specifically, the trophoblast cells cultured using a common culture plate were used as the control group, and the Experimental group was cultured in a plate coated with the extracellular matrix (procollagen, collagen, and fibronectin) prepared in Example 1. Further, the basal body temperature method and micro vibrating incubating conditions as shown in FIGS. 1 and 2 were applied for the Experimental group. The cells were sub-cultured every 3 days, and each culture supernatant was collected at the time of each subculture and the concentration of HLA-G molecules present in each culture supernatant was quantified using a Human HLA-G ELISA kit (LifeSpan BioSciences, Cat. #LS-F5033).

As a result, as shown in FIG. 3, when the cells were sub-cultured for 15 times each, in the control group, the concentration of HLA-G proteins found in the cultured supernatant collected after 3 passage was gradually decreased, and no expression of the HLA-G proteins was observed after 10 passages. In contrast, in the Experimental group, the concentration of HLA-G molecules found in the culture supernatant of trophoblast cells collected at the time of subculture after 5 passages was maintained at a level of 30 ng/ml or more.

Therefore, it was found that the trophoblast cells consecutively secreting and expressing HLA-G proteins could be produced when the temperature profiling based on the basal body temperature method, micro vibrating incubating conditions and the extracellular matrix were used.

Example 3: Preparation Method of Stem Cell Line in which Immune Tolerance Property was Induced Via Co-Culture with Trophoblast Cells Consecutively Secreting and Expressing HLA-G In Example 2, the trophoblast cells exhibiting immune tolerance property were prepared by consecutively secreting and expressing HLA-G. These trophoblast cells were used for the preparation of a stem cell line in which immune tolerance property was induced.

First, the trophoblast cells were cultured in a 6-well plate coated with the extracellular matrix prepared in Example 1. Herein, a serum-free DMEM low medium was used as the medium conditions, and mixed compositions (SigGrow™, Stemmedicare Inc., Korea), in which 30 kinds of mixed plant extracts and hPC were mixed at a ratio of 1:1, were used in an amount of 1.0 to 10 by weight based on the total weight of the medium, as shown in Table 4.

TABLE 4

Composition of Mixed Plant Extracts Contained in Cell Proliferation Medium

| No. | INCI Name | CAS No. |
|---|---|---|
| 1 | *Aspalathus Linearis* Leaf Extract | — |
| 2 | *Thuja Occidentalis* Leaf Extract | 90131-58-1 |
| 3 | *Melaleuca Alternifolia* (Tea Tree) Leaf Extract | 85085-48-9 |
| 4 | *Rosmarinus Officinalis* (Rosemary) Leaf Extract | 84604-14-8 |
| 5 | *Centella Asiatica* Extract | 84696-21-9 |
| 6 | *Salvia Officinalis* (Sage) Leaf Extract | 84082-79-1 |
| 7 | *Thymus Vulgaris* (Thyme) Extract | 84929-51-1 |
| 8 | *Melissa Officinalis* Leaf Extract | 84082-61-1 |
| 9 | *Hyssopus Officinalis* Extract | 84603-66-7 |
| 10 | *Origanum Majorana* Leaf Extract | 84082-58-6 |
| 11 | *Glycyrrhiza Uralensis* (Licorice) Root Extract | 94349-91-4 |
| 12 | *Angelica Gigas* Root Extract | — |
| 13 | *Cnidium Officinale* Root Extract | 168456-52-8 |
| 14 | *Paeonia Lactiflora* (Peonia) Root Extract | — |
| 15 | *Perilla Frutescens* Leaf Extract | 90082-61-4 |
| 16 | *Houttuynia Cordata* Extract | 164288-50-0 |
| 17 | *Camellia Sinensis* Leaf Extract | 84650-60-2 |
| 18 | *Poria Cocos* Extract | 168456-53-9 |
| 19 | *Panax Ginseng* Root Extract | 84650-12-4 |
| 20 | *Morus Alba* Bark Extract | 94167-05-2 |
| 21 | *Citrus Aurantifolia* (Lime) Fruit Extract | 90063-52-8 |
| 22 | *Citrus Limon* (Lemon) Fruit Extract | 84929-31-7 |
| 23 | *Vitis Vinifera* (Grape) Fruit Extract | 84929-27-1 |
| 24 | *Cucumis Melo* (Melon) Fruit Extract | 90063-94-8 |
| 25 | *Vaccinium Angustifolium* (Blueberry) Fruit Extract | — |
| 26 | *Prunus Mume* Fruit Extract | — |
| 27 | *Coffee Arabica* (Coffee) Seed Extract | 84650-00-0 |

TABLE 4-continued

Composition of Mixed Plant Extracts Contained
in Cell Proliferation Medium

| No. | INCI Name | CAS No. |
|---|---|---|
| 28 | *Sapindus Mukorossi* Fruit Extract | — |
| 29 | *Citrus Aurantium Dulcis* (Orange) Fruit Extract | 84012-28-2 |
| 30 | *Ananas Sativus* (Pineapple) Fruit Extract | — |

Simultaneously, among the human amniotic membrane-derived mesenchymal stem cells, human adipose-derived mesenchymal stem cells, human bone marrow-derived mesenchymal stem cells, human umbilical cord blood-derived mesenchymal stem cells and human amniotic fluid-derived mesenchymal stem cells, one type of stem cells was aliquoted into a 6-well multi-dish culture Nunc polycarbonate cell culture insert (ThermoFisher Scientific Inc., Rockford, Ill. USA, Cat. #140663) having a 3 μm pore size such that the trophoblast cells were positioned with a spacing of 0.9 mm in the 6-well plate (low position). Thereafter, the cells were cultured in a 5% $CO_2$ incubator for 3 to 4 days under the temperature profiling and vibrating incubating conditions applied in Example 2, and when the cells were proliferated about 70 to 90% in the plate, the sub-culture was performed at a ratio of 1:3.

Then, the secretion and expression of HLA-G proteins in the human-derived stem cells obtained at the time of sub-culture was confirmed by the following method. The stem cells were washed 2 to 3 times with D-PBS and centrifuged at 1,000 rpm for 5 minutes to remove all medium components. DMEM/F12, a serum-free medium, was added to a new flask, and the cells were inoculated at a cell density of 18,000 cells/cm$^2$ to 22,000 cells/cm$^2$ and cultured in a 5% $CO_2$ incubator at 37° C., and after 120 hours, the culture supernatant was collected. The concentration of HLA-G molecules present in each culture supernatant was quantified using a Human HLA-G ELISA kit in the same manner as in Example 2.

As a result, as shown in FIG. 4, when the sub-culture was performed for a total of 30 times, it was confirmed that HLA-G proteins were not detected in the culture supernatant of human-derived stem cells cultured alone instead of co-culture with trophoblast cells. In contrast, the concentration of HLA-G proteins gradually increased in the culture supernatant of the human-derived stem cells co-cultured with the trophoblast cells, as the sub-culture progressed, and after 10 passages of sub-culture, the concentration of HLA-G molecules found in the culture supernatant of the human-derived stem cell obtained at the time of the sub-culture was maintained at a level of 20 ng/ml or more. Furthermore, it was confirmed that HLA-G molecules were continuously present until 20 passages or more.

Based on the results above, it was found that when the stems cells were co-cultured with the trophoblast cells consecutively secreting and expressing HLA-G molecules prepared in Example 2 according to the method above, the novel stem cells line (hereinafter, referred to as MBTC-Cell™), in which immune tolerance property was induced by consecutively secreting and expressing HLA-G proteins, could be prepared.

Example 4: Preparation Method of Novel Stem Cell Line (MBTC-Cell™)-Derived Culture Medium In this Example, an extracellular vesicle derived from the novel stem cell line MBTC-Cell™, which was prepared in Example 3 and in which immune tolerance property was induced by consecutively secreting and expressing HLA-G proteins, and a protein composition, i.e., a culture medium, were prepared.

Extracellular vesicles are membrane vesicles that can be secreted out of cells in most animal and plant cells including stem cells. They can be classified into apoptotic bodies, microvesicles and exosomes according to size and secretion mechanism. The extracellular vesicles contain various miRNAs, mRNAs, cytokines, etc., depending on the characteristics of their parent cells, and play an important role in intercellular signaling and metabolism via these molecules. At the same time, it has been reported that the extracellular vesicles have therapeutic effects of their own and thus have gained much attention as an alternative to cell therapeutic agents, which have not solved the challenge of immune rejection. However, studies for developing therapeutic agents using exosomes and microvesicles are limited to the laboratory level, for example, they are restrictively used in the field of disease diagnosis using exosomes, which are present in a small amount in the blood, it is almost impossible to isolate exosomes with a purity in a clinically applicable level, and a method of isolating only clinically applicable microvesicles has not been developed. Further, even when the extracellular vesicles are applied for therapeutic purposes, there is a possibility that an immune rejection may be induced by various antigenic markers present in the membrane of the extracellular vesicles having the characteristics of their parent cells. Accordingly, in order to solve this problem, the present inventor has made efforts to confirm the immune tolerance of the extracellular vesicles contained in the culture medium derived from the novel stem cell line prepared in Example 3 above.

Specifically, the MBTC-Cell™ was inoculated at a density of 18,000 cells/cm$^2$ to 22,000 cells/cm$^2$ in DMEM/F12, a serum-free medium, and cultured in a 5% $CO_2$ incubator at 37° C. for 120 hours to collect the culture supernatant. The collected supernatant was filtered through a 0.8 μm filter (MCE MF-Millipore™) to remove all cell debris and dead cells, thereby obtaining an extracellular vesicle (MBTC-EV™) containing all MBTC-Cell™-derived exosomes and microvesicles, and a protein composition.

In order to confirm the contamination thereof with microorganisms and viruses, an Adventitious Virus Test and Microbial Residual Test were performed in accordance with the approval criteria for cell therapeutic agents in the Ministry of Food and Drug Safety, and as a result, it was confirmed that the MBTC-Cell™-derived extracellular vesicle (MBTC-EV™) and the protein composition did not contain exogenous viruses and microorganisms.

In addition, as can be seen from FIG. 5, as a result of observing the MBTC-Cell™-derived culture medium under a scanning electron microscope (SEM, Hitachi S-4800), it was confirmed that the microvesicles and exosomes having various sizes coexisted.

Example 5: Confirmation of Proteins Contained in MBTC-Cell™-Derived Culture Medium In order to confirm the components contained in the MBTC-Cell™-derived culture medium prepared in Example 4 in detail, quantitative and qualitative analyses were performed on the proteins contained therein. Meanwhile, as the control group, a culture medium in which the human-derived mesenchymal stem cells were cultured alone was used.

Specifically, the proteins were quantified using an BCA assay for the control and the Experimental groups, and 100 µg of the proteins were lyophilized and then subjected to mass spectrometry, respectively. Protein identification and absolute quantification were performed based on the results obtained by mass spectrometry using ProteinLynx Global Server (PLGS)™ Ver. 3.0 (integrated mass-informatics platform). The protein identification was performed using the human database of International Protein Index (Ver. 3.87) and absolute quantification was performed based on the mass value of the standard product BSA (SwissProt P2769).

As a result, as can be seen from FIG. 6, it was confirmed that the total protein contents contained in the culture medium produced by culturing the human amniotic membrane-derived mesenchymal stem cells (hAM-MSC), human bone marrow-derived mesenchymal stem cells (hBM-MSC), human umbilical cord blood-derived mesenchymal stem cells (HUMSC), human amniotic fluid-derived mesenchymal stem cells (hAF-MSC), and human adipose-derived mesenchymal stem cells (hADSC) alone were 29.91 µg/mL, 23.37 µg/mL, 19.89 µg/mL, 51.36 µg/mL, and 20.16 µg/mL, respectively. In contrast, the total protein contents contained in the culture medium produced from the human amniotic membrane-derived MBTC-Cell™ (hAM-MSC derived MBTC-Cell™), human bone marrow-derived MBTC-Cell™ (hBM-MSC derived MBTC-Cell™), human umbilical cord blood-MBTC-Cell™ (HUMSC derived MBTC-Cell™), human amniotic fluid-derived MBTC-Cell™ (hAF-MSC derived MBTC-Cell™), and human adipose-derived MBTC-Cell™ (hADSC derived MBTC-Cell™), which are novel stem cell lines prepared in Example 4, were 236.32 µg/mL, 189.13 µg/mL, 195.28 µg/mL, 211.70 µg/mL, and 178.53 µg/mL, respectively, confirming that the total protein contents were increased by 790%, 809%, 982%, 412%, and 886% compared to the control group, respectively.

In addition, as shown in FIG. 7, each MBTC-Cell™-derived culture medium was qualitatively analyzed, and as a result, it was confirmed that about 520 kinds of the same protein components were contained therein and that 600 kinds of other proteins were similar types to each other.

From the above results, it can be seen that each MBTC-Cell™-derived culture medium had a significantly higher total protein content than that of common stem cell culture medium and that each MBTC-Cell™ secretes similar kinds of proteins even though the stem cells had different origins.

Example 6: Analysis of Protein Components Contained in MBTC-Cell™-Derived Culture Medium

Example 6-1: Proteins Related to Immune Tolerance

Among the proteins contained in the MBTC-Cell™-derived culture medium (Experimental group) prepared in Example 5, first, it was examined whether proteins related to immune tolerance were contained. Meanwhile, as the control group, a culture medium in which the human-derived mesenchymal stem cells were cultured alone was used.

Specifically, the proteins were quantified using an BCA assay for the control and the Experimental groups, and 100 µg of the proteins were lyophilized and subjected to mass spectrometry, respectively.

As a result, as shown in Table 5, it was confirmed that the Experimental Group contained about 4 to 8 times higher contents of the proteins related to immune tolerance than the control group.

TABLE 5

Comparison of Contents of Proteins Related to Immune Tolerance

| | Name of Antibody | Name of Protein | Content (ng/mL) | |
|---|---|---|---|---|
| | | | Control Group | Experimental Group |
| 1 | FSCN1 | Fascin | 0.617 | 4.293 |
| 2 | LGALS3 | Galectin-3 | 0.527 | 3.734 |
| 3 | LGALS3BP | Galectic-3-binding Protein | 4.711 | 34.105 |
| 4 | Cyclophilin | Peptidylprolyl cis-trans isomerase B | 0.454 | 3.598 |
| 5 | FOXP3 | Forkhead box P3 | 0.317 | 2.390 |
| 6 | IL-10 | Interleukin-10 | 0.551 | 2.370 |
| 7 | TGF beta1 | Transforming growth factor beta-1 | 0.486 | 2.350 |

Example 6-2: Analysis of Proteins Related to Recovering Proteasome Function Among the proteins contained in the MBTC-Cell™-derived culture medium (Experimental group) prepared in Example 5, it was examined whether proteins related to recovering proteasome function were contained. Meanwhile, as the control group, a culture medium in which the human-derived mesenchymal stem cells were cultured alone was used.

Specifically, for the control and Experimental groups, protein mass spectrometry was carried out by the method according to Example 6-1, respectively.

As a result, as shown in Table 6, it was confirmed that the Experimental group contained about 3 to 16 times higher contents of the protein related to recovering proteasome function than the control group and that new proteins that were not found in the control group were also expressed.

TABLE 6

Comparison of Contents of Proteins Related to Recovering Proteasome Function

| | Name of Antibody | Name of Protein | Content (ng/mL) | |
|---|---|---|---|---|
| | | | Control Group | Experimental Group |
| 1 | PSMC8 | 26S protease regulatory subunit 8 | — | 0.162 |
| 2 | PSMD2 | 26S proteasome non-ATPase regulatory subunit 2 | | 0.346 |

TABLE 6-continued

Comparison of Contents of Proteins Related to Recovering Proteasome Function

| | Name of Antibody | Name of Protein | Content (ng/mL) Control Group | Content (ng/mL) Experimental Group |
|---|---|---|---|---|
| 3 | PSMD3 | 26S proteasome non-ATPase regulatory subunit 3 | 3.713 | 293.877 |
| 4 | PSMD6 | 26S proteasome non-ATPase regulatory subunit 6 | 0.571 | 14.209 |
| 5 | HS71L | Heat shock 70 kDa protein 1L | 1.345 | 30.678 |
| 6 | PSMC6 | 26S proteasome regulatory subunit S10B | — | 0.023 |
| 7 | RNF40 | E3 ubiquitin-protein ligase BRE1B | 2.664 | 38.697 |
| 8 | HSP76 | Heat shock 70 kDa protein 6 | 2.140 | 46.257 |
| 9 | HSP90Bb | Heat shock 70 kDa protein 90Bb | — | 7.127 |
| 10 | HSP27 | Heat shock protein beta-1 | 3.697 | 59.562 |
| 11 | HSP90b | Heat shock protein beta-90 | 5.841 | 163.066 |
| 12 | HSPA2 | Heat shock-related 70 kDa protein 2 | 2.014 | 50.585 |
| 13 | HSPA8 | Heat shock-related 70 kDa protein 8 | 1.068 | 73.012 |
| 14 | PSMD1 | 26S proteasome non-ATPase regulatory subunit 1 | 3.215 | 48.998 |
| 15 | PSMA1 | Proteasome subunit alpha type-1 | 6.997 | 110.504 |
| 16 | PSMA2 | Proteasome subunit alpha type-2 | — | 3.551 |
| 17 | PSMA5 | Proteasome subunit alpha type-5 | 3.547 | 18.875 |
| 18 | PSMB4 | Proteasome subunit beta type-4 | 0.697 | 4.520 |
| 19 | PSMA6 | Proteasome subunit alpha type-6 | 1.547 | 5.817 |
| 20 | PSMA7 | Proteasome subunit alpha type-7 | 0.647 | 9.693 |
| 21 | PSMB5 | Proteasome subunit beta type-5 | — | 2.772 |
| 22 | PSMB8 | Proteasome subunit beta type-8 | — | 1.830 |
| 23 | PSMB1 | Proteasome subunit beta type-1 | — | 2.592 |
| 24 | PSMB2 | Proteasome subunit beta type-2 | — | 2.951 |
| 25 | PSMB3 | Proteasome subunit beta type-3 | — | 2.931 |
| 26 | UBA1 | Ubiquitin-like modifier-activating enzyme 1 | 1.697 | 24.037 |

Example 6-3: Analysis of Proteins Related to Recovering Autophagy Function

Among the proteins contained in the MBTC-Cell™-derived culture medium (Experimental group) prepared in Example 5, it was examined whether proteins related to recovering autophagy function were contained. Meanwhile, as the control group, a culture medium in which the human-derived mesenchymal stem cells were cultured alone was used.

Specifically, for the control and Experimental groups, protein mass spectrometry was carried out by the method according to Example 6-1, respectively.

As a result, as shown in Table 7, it was confirmed that the Experimental group contained about 4 to 27 times higher contents of proteins related to recovering autophagy function than the control group and that new proteins that were not found in the control group were also expressed.

TABLE 7

Comparison of Analysis of Proteins Related to Recovering Autophagy Function

| | Name of Antibody | Name of Protein | Content (ng/mL) Control Group | Content (ng/mL) Experimental Group |
|---|---|---|---|---|
| 1 | BAD | Bcl2-associated agonist of cell death | 2.894 | 186.5 |
| 2 | IKK-gamma | NF-kappa-B essential modulator | 3.247 | 193.0 |
| 3 | Insulin | Insulin | 7.598 | 134.5 |
| 4 | EGF | Pro-epidermal growth factor | 16.547 | 148.5 |
| 5 | HGH | Somatotropin | 29.327 | 130.0 |
| 6 | TGF beta2 | Transforming growth factor beta-2 | 14.015 | 146.0 |
| 7 | IL-1 beta | Interleukin-1 beta | 10.369 | 157.0 |

TABLE 7-continued

Comparison of Analysis of Proteins Related to Recovering Autophagy Function

| | Name of Antibody | Name of Protein | Content (ng/mL) Control Group | Content (ng/mL) Experimental Group |
|---|---|---|---|---|
| 8 | LAMP2 | Lysosomal-associated membrane protein 2 | — | 4.246 |
| 9 | ATG16L2 | Autophagy-related protein 16-2 | 4.117 | 67.144 |
| 10 | ATG9A | Autophagy-related protein 9A | — | 0.118 |
| 11 | M6P | Mannose-6-phosphate | 3.476 | 93.180 |

Example 6-4: Analysis of Proteins Related to Recovering Macrophage-Phagocytosis Function Among the proteins contained in the MBTC-Cell™-derived culture medium (Experimental group) prepared in Example 5, it was examined whether proteins related to recovering macrophage-phagocytosis function were contained. Meanwhile, as the control group, a culture medium in which the human-derived mesenchymal stem cells were cultured alone was used.

Specifically, for the control and Experimental groups, protein mass spectrometry was carried out by the method according to Example 6-1, respectively.

As a result, as shown in Table 8, it was confirmed that the Experimental group contained about 7 to 45 times higher contents of proteins related to recovering macrophage-phagocytosis function than the control group and that new proteins that were not found in the control group were also expressed.

TABLE 8

Comparison of Analysis of Antioxidant Proteins Related to Recovering Macrophage-Phagocytosis Function

|  | Name of Antibody | Name of Protein | Content (ng/mL) Control Group | Content (ng/mL) Experimental Group |
|---|---|---|---|---|
| 1 | GSTO1 | Glutathione S-transferase omega-1 | — | 5.501 |
| 2 | GR | Glutathione reductase | — | 1.648 |
| 3 | PRDX1 | Peroxiredoxin-1 | 3.647 | 62.662 |
| 4 | PRDX2 | Peroxiredoxin-2 | 0.448 | 16.194 |
| 5 | PRDX4 | Peroxiredoxin-4 | — | 6.355 |
| 6 | PRDX6 | Peroxiredoxin-6 | 5.716 | 45.358 |
| 7 | SOD | Superoxide dismutase | 0.037 | 1.668 |

Example 6-5: Analysis of Proteins Related to Maintaining Intracellular Signaling Homeostasis Among the proteins contained in the MBTC-Cell™-derived culture medium (Experimental group) prepared in Example 5, it was examined whether proteins related to maintaining intracellular signaling homeostasis were contained. Meanwhile, as the control group, a culture medium in which the human-derived mesenchymal stem cells were cultured alone was used.

Specifically, for the control and the Experimental group, protein mass spectrometry was carried out by the method according to Example 6-1, respectively.

As a result, as shown in Table 9, it was confirmed that the Experimental group contained about 49 times higher contents of proteins related to maintaining intracellular signaling homeostasis than the control group and that new proteins that were not found in the control group were also expressed.

TABLE 9

Comparison of Analysis of Proteins Related to Maintaining Intracellular Signaling Homeostasis

|  | Name of Antibody | Name of Protein | Content (ng/mL) Control Group | Content (ng/mL) Experimental Group |
|---|---|---|---|---|
| 1 | PTEN | Phosphatase and tensin homolog | 0.047 | 2.331 |
| 2 | SHIP1 | SH2 (Src homology 2)-containing inositol phosphatase-1 | — | 2.600 |
| 3 | GSK-3b | Glycogen synthase kinase 3 beta | — | 2.378 |

Example 7: Verification of Anti-Aging, Antioxidant, and Macrophage-Phagocytosis Recovery Effects of MBTC-Cell™-Derived Culture Medium

Example 7-1: Verification of Anti-Aging Effect

Since it was confirmed that the MBTC-Cell™-derived culture medium prepared in Example 5 contains large amounts of proteins related to immune tolerance, proteins related to recovering proteasome function, proteins related to recovering autophagy function, proteins related to recovering macrophage-phagocytosis function, or proteins related to maintaining intracellular signaling homeostasis, based on this finding, it was examined whether the culture medium exhibited physiological effects such as anti-aging.

Specifically, the control group was 0.9% saline; Experimental Group 1 was a culture medium prepared by culturing human-derived mesenchymal stem cells alone; and Experimental Group 2 was the MBTC-Cell™-derived culture medium. Four mice were used per group, and 100 μL of the samples were intravenously administered per mouse, and then the body weight, and the amount of water and feed intake were measured for 3 days. After 3 days, the anti-aging effect was confirmed by visual examination and blood test through autopsy.

As a result, as shown in FIG. 8, there were no significant changes in the body weight, and the amount of water and feed intake according to the administration of the samples in the control group, and Experimental Groups 1 and 2, and an increase and decrease were observed within the normal range. In addition, the autopsy results showed no abnormalities in both the control and Experimental groups.

In addition, as shown in FIG. 9, the expression levels of growth hormone and insulin-like growth factor 1 (IGF-1), which are representative anti-aging-related biomarkers, were compared, and as a result, it was confirmed that there was a remarkable increase of about 20% to 30% in Experimental Group 2 compared to the control group and Experimental Group 1.

From these results, it can be concluded that the MBTC-Cell™-derived culture medium showed an excellent anti-aging effect.

Example 7-2: Verification of Antioxidant Effect

Further, it was examined whether the MBTC-Cell™-derived culture medium had an antioxidant effect.

Specifically, the control group, Experimental Group 1, and Experimental Group 2 were determined in the same manner as in Example 7-1, and the serum GSH/GSSH ratio, which is a typical antioxidation-related biomarker, was measured after administration of the culture medium to mice.

As a result, as shown in FIG. 10, it was confirmed that the serum GSH/GSSH (glutathione/glutathione disulfide) ratio increased about 10% in Experimental Group 2 compared to the control group and Experimental Group 1.

From these results, it can be concluded that the MBTC-Cell™-derived culture medium showed an excellent antioxidant effect.

Example 7-3: Verification of Macrophage-Phagocytosis Recovery Effect

In addition, it was examined whether the MBTC-Cell™-derived culture medium showed macrophage-phagocytosis recovery effect.

Specifically, the control group, Experimental Group 1, and Experimental Group 2 were determined in the same manner as in Example 7-1, and after administering the mice with the samples, the concentrations of serum LDL-cholesterol and HDL-cholesterol, which are representative biomarkers related to the macrophage-phagocytosis recovery, were measured. In this experiment, the LDL-cholesterol reagent (Bayer, USA) and direct HDL-cholesterol reagent (Bayer, USA) were used, and the concentrations thereof were measured using an automated hematology analyzer (ADVIA 1650, Bayer, Japan).

As a result, as shown in FIG. 11, the serum LDL cholesterol concentration was remarkably reduced by about 2.88 mg/dL and 2.55 mg/dL in Experimental Group 2, as compared to the control group and Experimental Group 1, respectively. In contrast, the concentration of HDL cholesterol was remarkably increased by about 3.83 mg/dL and 3.1 mg/dL in Experimental Group 2 as compared to the control group and Experimental Group 1, respectively.

From these results, it can be concluded that the MBTC-Cell™-derived culture medium showed a macrophage-phagocytosis recovery effect of favorably regulating serum cholesterol.

Example 8. Confirmation of Secretory Characteristics of HLA-G5 Proteins Contained in Trophoblast Culture Medium In order to confirm the secretory characteristics of HLA-G5 proteins contained in the trophoblast cell culture medium prepared according to the present invention, the trophoblast cells were cultured in the same manner as in Example 2, and the HLA-G5 proteins contained in the culture supernatant was analyzed by ELISA. In addition, the culture supernatant of the trophoblast cells was compared with the culture medium (control group) of the cells cultured by the conventional method.

Herein, the ELISA was performed by an ELISA kit (MBS267094, MyBiosource) using an 5A6G7 antibody to selectively detect HLA-G5 proteins that were secreted and expressed outside the cells. The results are shown in FIG. 12.

As a result, as can be seen from FIG. 12, the concentration of HLA-G5 proteins contained in the culture supernatant of the trophoblast cells cultured by the conventional culture method gradually decreased as the subculture progressed. In contrast, the concentration of HLA-G5 proteins (Experimental group) contained in the culture supernatant of trophoblast cells cultured under the human body-like culture conditions of the present invention gradually increased as the subculture progressed.

From these results, it was concluded that the trophoblast cells prepared according to the present invention secreted HLA-G5 proteins outside of the trophoblast cells, and the amount of the HLA-G5 proteins increased as the subculture progressed in the culture supernatant, thereby confirming that the HLA-G5 proteins were consecutively secreted and expressed.

Example 9. Confirmation of Secretory Characteristics of HLA-G5 Proteins Contained in Stem Cell Culture Medium In order to confirm the secretory characteristics of the HLA-G5 proteins contained in the stem cell culture medium in which immune tolerance property was induced by co-culturing with the trophoblast cells cultured under the human body-like under conditions as the present invention, the HLA-G5 proteins contained in the culture supernatant obtained by culturing the mesenchymal stem cells in the same manner as Example 3 were analyzed by ELISA. Herein, the ELISA was performed by an ELISA kit (MBS267094, MyBiosource) using an 5A6G7 antibody to selectively detect HLA-G5 proteins that were secreted and expressed outside the cells. The results are shown in FIG. 13.

As a result, as can be seen from FIG. 13, the concentration of HLA-G5 proteins contained in the culture supernatant gradually increased as the subculture progressed.

That is, from these results, it was confirmed that the HLA-G5 proteins secreted and expressed from the stem cells prepared according to the present invention could be in the form that can be secreted and expressed outside the cells, and that the stem cells had the feature of consecutively secreting and expressing HLA-G5 proteins.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description, and it should be understood that all modifications or variations derived from the meanings and scope of the present invention and equivalents thereof are included in the scope of the appended claims.

The invention claimed is:

1. A method of preparing a culture medium of mesenchymal stem cells consecutively secreting and expressing human leukocyte antigen G (HLA-G) proteins, comprising:
   (1) preparing trophoblast cells continuously secreting and expressing HLA-G proteins by the steps of:
   (1a) culturing trophoblast cells under a human body-like culture condition, wherein the human body-like culture condition includes a 15-day period temperature condition within a range of 36.3° C. to 37.2° C., based on a basal body temperature method, in which the temperature 36.5° C. at Day 1, 36.6° C. at Day 2, 36.7° C. at Day 3, 36.7° C. at Day 4, 36.6° C. at Day 5, 36.7° C. at Day 6, 36.6° C. at Day 7, 36.3° C. at Day 8, 36.9° C. at Day 9, 37.1° C. at Day 10, 37.1° C. at Day 11, 37.0° C. at Day 12, 37.2° C. at Day 13, 37.1° C. at Day 14, and 37.0° C. at Day 15, a 24-hour period vibrating incubating condition varied within a range of 10 revolutions per minute (RPM) to 30 RPM, in which the vibrating incubation is 10 RPM at 0 hour to 8 hours, 15 RPM at 9 hours, 20 RPM at 10 hours, 25 RPM at 11 hours, 30 RPM at 12 hours to 19 hours, 25 RPM at 20 hours, 20 RPM at 21 hours, 15 RPM at 22 hours, 10 RPM at 23 hours to 24 hours, and using a cell culture plate containing an extracellular matrix; and
   (1b) sub-culturing the cultured trophoblast cells;
   (2) preparing mesenchymal stem cells continuously secreting and expressing HLA-G proteins by the steps of:
   (2a) co-culturing mesenchymal stem cells with the trophoblast cells consecutively secreting and expressing HLA-G proteins; and
   (2b) sub-culturing the cultured mesenchymal stem cells; and
   (3) preparing a culture medium from the cultured mesenchymal stem cells of step (2b), comprising:
   (3a) inoculating the mesenchymal stem cells obtained at the time of sub-culturing during the preparation of the mesenchymal stem cells at a density of 18,000 cells/$cm^2$ to 22,000 cells/$cm^2$ into serum-free medium;
   (3b) culturing the mesenchymal stem cells in the serum-free medium for 114 hours to 126 hours: and
   (3c) obtaining the culture supernatant.

2. The method of claim 1, wherein the mesenchymal stem cells are derived from fat, bone marrow, umbilical cord blood, amniotic fluid or amniotic membrane.

3. The method of claim 1, wherein the prepared mesenchymal stem cell culture medium contains extracellular vesicles.

4. The method of claim 3, wherein the extracellular vesicles are at least one selected from the group consisting of an apoptotic body, a microvesicle, and an exosome.

5. The method of claim 3, wherein the prepared mesenchymal stem cell culture medium has an increased total protein content as compared to a culture medium in which the mesenchymal stem cells are cultured alone.

6. The method of claim 5, wherein the protein is a protein related to immune tolerance, a protein related to recovering proteasome function, a protein related to recovering autophagy function, an antioxidant protein related to recovering macrophage-phagocytosis function, or a protein related to maintaining intracellular signaling homeostasis.

7. The method of claim 6, wherein the protein related to immune tolerance is fascin, galectin-3, galectic-3-binding protein, peptidylprolyl cis-trans isomerase B, forkhead box P3, interleukin-10, or transforming growth factor beta-1;

wherein the protein related to recovering proteasome function is 26S protease regulatory subunit 8, 26S proteasome non-ATPase regulatory subunit 2, 26S proteasome non-ATPase regulatory subunit 3, 26S proteasome non-ATPase regulatory subunit 6, heat shock 70 kDa protein 1L, 26S proteasome regulatory subunit S10B, E3 ubiquitin-protein ligase BRE1B, heat shock 70 kDa protein 6, heat shock 70 kDa protein 90Bb, heat shock protein beta-1, heat shock-related 70 kDa protein 2, heat shock-related 70 kDa protein 8, 26S proteasome non-ATPase regulatory subunit 1, proteasome subunit alpha type-1, proteasome subunit alpha type-2, proteasome subunit alpha type-5, proteasome subunit beta type-4, proteasome subunit alpha type-6, proteasome subunit alpha type-7, proteasome subunit beta type-5, proteasome subunit beta type-8, proteasome subunit beta type-1, proteasome subunit beta type-2, proteasome subunit beta type-3, or ubiquitin-like modifier-activating enzyme 1;

wherein the protein related to recovering autophagy function is B-cell lymphoma 2 (Bcl2-) associated agonist of cell death, NF-kappa-B essential modulator, insulin, pro-epidermal growth factor, somatotropin, transforming growth factor beta-2, interleukin-1 beta, lysosomal associated membrane protein 2, autophagy-related protein 16-2, autophagy-related protein 9A, or mannose-6 phosphate; and wherein the protein related to maintaining intracellular signaling homeostasis is phosphatase and tensin homolog, SH2 (Src homology 2)-containing inositol phosphatase-1, or glycogen synthase kinase 3 beta.

8. The method of claim 1, wherein the extracellular matrix is at least one selected from the group consisting of collagen, fibronectin, and procollagen in the steps of (1).

9. The method of claim 8, further comprising preparing the extracellular matrix prior to use by the steps of:
(a) inoculating fibroblasts at a density of 18,000 cells/cm$^2$ to 22,000 cells/cm$^2$;
(b) culturing the fibroblasts in a serum-free medium; and
(c) obtaining a fibroblast culture medium containing the extracellular matrix after culturing for 114 hours to 126 hours,
wherein the serum-free medium contains 15% (v/v) to 25% (v/v) of a human mesenchymal stem cell-derived protein.

10. The method of claim 9, further comprising preparing the human mesenchymal stem cell-derived protein by the steps of:
(a) inoculating human mesenchymal stem cells at a density of 18,000 cells/cm$^2$ to 22,000 cells/cm$^2$;
(b) culturing the stem cells in a serum-free medium; and
(c) obtaining a stem cell culture medium containing the human mesenchymal stem cell-derived protein after culturing for 114 hours to 126 hours.

11. The method of claim 1, wherein the sub-culture is performed for 5 passages to 15 passages in the steps of (1b).

12. The method of claim 1, wherein the HLA-G proteins are maintained at 30 ng/ml or more in the steps of (1).

13. The method of claim 1, wherein the mesenchymal stem cell is derived from fat, bone marrow, umbilical cord blood, amniotic fluid, or amniotic membrane in the steps of (2).

14. The method of claim 1, wherein the sub-culture is performed for 10 passages to 30 passages in the steps of (2b).

15. The method of claim 1, wherein the HLA-G proteins contained in the prepared mesenchymal stem cells are present in a culture supernatant and a cell surface in the steps of (2).

16. The method of claim 1, wherein the HLA-G proteins contained in the prepared mesenchymal stem cells are maintained at 20 ng/ml or more in the steps of (2).

17. The method of claim 1, wherein the co-culture is performed in a medium comprising a mixture in which a human mesenchymal stem cell-derived protein and a plant extract are mixed at a ratio of 1:0.5 to 1:1.5 in the steps of (2a).

18. The method of claim 17, wherein the plant extract is a *Aspalathus linearis* leaf extract, *Thuja occidentalis* leaf extract, *Melaleuca alternifolia* (tea tree) leaf extract, *Rosmarinus officinalis* (rosemary) leaf extract, *Centella asiatica* extract, *Salvia officinalis* (sage) leaf extract, *Thymus vulgaris* (thyme) extract, *Melissa officinalis* leaf extract, *Hyssopus officinalis* extract, *Origanum majorana* leaf extract, *Glycyrrhiza uralensis* (licorice) root extract, *Angelica gigas* root extract, *Cnidium officinale* root extract, *Paeonia lactiflora* (peonia) root extract, *Perilla frutescens* leaf extract, *Houttuynia cordata* extract, *Camellia sinensis* leaf extract, *Poria cocos* extract, *Panax ginseng* root extract, *Morus alba* bark extract, *Citrus aurantifolia* (lime) fruit extract, *Citrus limon* (lemon) fruit extract, *Vitis vinifera* (grape) fruit extract, *Cucumis melo* (melon) fruit extract, *Vaccinium angustifolium* (blueberry) fruit extract, *Prunus mume* fruit extract, *Coffee arabica* (coffee) seed extract, *Sapindus mukorossi* fruit extract, *Citrus aurantium dulcis* (orange) fruit extract, *Ananas sativus* (pineapple) fruit extract, or a combination thereof.

* * * * *